US009660324B2

(12) United States Patent
Baringer

(10) Patent No.: US 9,660,324 B2
(45) Date of Patent: May 23, 2017

(54) HYBRID PIEZOELECTRIC DEVICE / RADIO FREQUENCY ANTENNA

(71) Applicant: Fitbit, Inc., San Francisco, CA (US)

(72) Inventor: William B. Baringer, Piedmont, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/880,706

(22) Filed: Oct. 12, 2015

(65) Prior Publication Data

US 2016/0036119 A1   Feb. 4, 2016

Related U.S. Application Data

(63) Continuation of application No. 14/444,944, filed on Jul. 28, 2014, now Pat. No. 9,196,964, which is a
(Continued)

(51) Int. Cl.
*H01Q 1/24* (2006.01)
*H01Q 1/22* (2006.01)
(Continued)

(52) U.S. Cl.
CPC ............ *H01Q 1/22* (2013.01); *A61B 5/0002* (2013.01); *A61B 5/02416* (2013.01); *A61B 5/02427* (2013.01); *A61B 5/02433* (2013.01); *A61B 5/02438* (2013.01); *A61B 5/1123* (2013.01); *A61B 5/4812* (2013.01); *B06B 1/0644* (2013.01); *H01L 41/08* (2013.01); *H01L 41/09* (2013.01); *H01L 41/25* (2013.01); *H01L 41/312* (2013.01); *H01Q 1/273* (2013.01);
(Continued)

(58) Field of Classification Search
CPC ........ H01Q 9/0421; H01Q 1/24; H01Q 1/273; H01Q 21/28
See application file for complete search history.

(56) References Cited

U.S. PATENT DOCUMENTS 6,127,799 A    10/2000  Krishnan
6,583,369 B2   6/2003   Montagnino et al.
(Continued)

FOREIGN PATENT DOCUMENTS

CN    103199333    7/2013
CN    203644061    6/2014
(Continued)

OTHER PUBLICATIONS

U.S. Appl. No. 14/880,703, filed Oct. 12, 2015, Baringer et al.
(Continued)

*Primary Examiner* — Hoang Nguyen
(74) *Attorney, Agent, or Firm* — Weaver Austin Villeneuve & Sampson LLP

(57) ABSTRACT

A hybrid antenna including a piezoelectric device and an RF radiator. The hybrid antenna is capable of providing both RF and piezoelectric device functionality, e.g., radio frequency transmission/reception capabilities for radio frequency devices as well as sound-producing and/or energy-scavenging functionality via the piezoelectric device. The piezoelectric device may be in conductive contact with the RF radiator or may not be in conductive contact with the RF radiator.

29 Claims, 15 Drawing Sheets

Related U.S. Application Data continuation-in-part of application No. 14/290,906, filed on May 29, 2014, now Pat. No. 9,520,638.

(60) Provisional application No. 61/948,470, filed on Mar. 5, 2014.

(51) Int. Cl.

| | | |
|---|---|---|
| *H01Q 9/04* | (2006.01) | |
| *H01Q 1/27* | (2006.01) | |
| *A61B 5/00* | (2006.01) | |
| *A61B 5/024* | (2006.01) | |
| *A61B 5/11* | (2006.01) | |
| *H01Q 21/28* | (2006.01) | |
| *H04W 4/02* | (2009.01) | |
| *H01L 41/08* | (2006.01) | |
| *H01L 41/25* | (2013.01) | |
| *H01L 41/312* | (2013.01) | |
| *H01Q 1/48* | (2006.01) | |
| *B06B 1/06* | (2006.01) | |
| *H01L 41/09* | (2006.01) | |
| *H04W 4/00* | (2009.01) | |
| *H04L 29/08* | (2006.01) | |

(52) U.S. Cl.
CPC ............. *H01Q 1/48* (2013.01); *H01Q 9/0407* (2013.01); *H01Q 9/0421* (2013.01); *H01Q 21/28* (2013.01); *H04W 4/027* (2013.01); *H04L 67/12* (2013.01); *H04W 4/008* (2013.01); *Y10T 29/42* (2015.01); *Y10T 29/49016* (2015.01)

(56) References Cited

U.S. PATENT DOCUMENTS

| | | | |
|---|---|---|---|
| 6,744,367 B1 * | 6/2004 | Forster ............... | G06K 19/0675 310/313 R |
| 6,856,291 B2 | 2/2005 | Mickle et al. | |
| 7,679,514 B2 | 3/2010 | Rofougaran et al. | |
| 8,208,867 B2 | 6/2012 | Lum et al. | |
| 8,390,249 B2 | 3/2013 | Walley et al. | |
| 8,497,658 B2 | 7/2013 | Von Novak et al. | |
| 8,610,638 B2 | 12/2013 | Larsen et al. | |
| 8,653,927 B2 | 2/2014 | Singh et al. | |
| 8,686,685 B2 | 4/2014 | Moshfeghi | |
| 9,196,964 B2 | 11/2015 | Baringer | |
| 2004/0171403 A1 | 9/2004 | Mikkola | |
| 2004/0233108 A1 | 11/2004 | Bordi | |
| 2005/0024273 A1 | 2/2005 | Hayes | |
| 2007/0132641 A1 | 6/2007 | Korva et al. | |
| 2008/0068177 A1 | 3/2008 | Copeland | |
| 2008/0081631 A1 | 4/2008 | Rofougaran | |
| 2008/0081632 A1 | 4/2008 | Malik | |
| 2008/0143610 A1 | 6/2008 | Wang et al. | |
| 2008/0272889 A1 | 11/2008 | Symons | |
| 2009/0312046 A1 | 12/2009 | Clevenger et al. | |
| 2010/0190436 A1 | 7/2010 | Cook et al. | |
| 2010/0331145 A1 | 12/2010 | Lakovic et al. | |
| 2011/0032105 A1 | 2/2011 | Hoffman et al. | |
| 2011/0090126 A1 | 4/2011 | Szini et al. | |
| 2011/0095947 A1 | 4/2011 | Chou | |
| 2011/0115303 A1 | 5/2011 | Baarman | |
| 2011/0136430 A1 | 6/2011 | Konya | |
| 2011/0217927 A1 | 9/2011 | Ben-Shalom et al. | |
| 2011/0278947 A1 | 11/2011 | Hennig et al. | |
| 2011/0294537 A1 | 12/2011 | Vance | |
| 2011/0309904 A1 | 12/2011 | Aoki | |
| 2012/0001705 A1 | 1/2012 | Nozue et al. | |
| 2012/0001823 A1 | 1/2012 | Peters et al. | |
| 2012/0123273 A1 | 5/2012 | Okuno et al. | |
| 2012/0194393 A1 | 8/2012 | Uttermann et al. | |
| 2012/0226197 A1 | 9/2012 | Sanders et al. | |
| 2012/0274508 A1 | 11/2012 | Brown et al. | |
| 2013/0093383 A1 | 4/2013 | Kim et al. | |
| 2013/0093387 A1 | 4/2013 | Vassilieff et al. | |
| 2013/0101149 A1 | 4/2013 | Maenpaa | |
| 2013/0106684 A1 | 5/2013 | Weast et al. | |
| 2013/0127404 A1 | 5/2013 | Maenpaa | |
| 2014/0002318 A1 | 1/2014 | Meulmester et al. | |
| 2014/0099614 A1 | 4/2014 | Hu et al. | |
| 2014/0117928 A1 | 5/2014 | Liao | |
| 2014/0266939 A1 | 9/2014 | Baringer et al. | |
| 2015/0255871 A1 | 9/2015 | Baringer | |
| 2016/0036118 A1 | 2/2016 | Baringer et al. | |

FOREIGN PATENT DOCUMENTS

| | | |
|---|---|---|
| EP | 1 897 231 | 9/2009 |
| EP | 1 721 237 | 8/2012 |

OTHER PUBLICATIONS

US Office Action, dated Jan. 28, 2015 issued in U.S. Appl. No. 14/290,906.

US Final Office Action, dated May 27, 2015 issued in U.S. Appl. No. 14/290,906.

US Office Action, dated Oct. 2, 2015 issued in U.S. Appl. No. 14/290,906.

US Office Action, dated Feb. 2, 2015 issued in U.S. Appl. No. 14/444,944.

US Final Office Action, dated Jun. 3, 2015 issued in U.S. Appl. No. 14/444,944.

US Notice of Allowance, dated Oct. 6, 2015 issued in U.S. Appl. No. 14/444,944.

"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pages.

Bhuyan et al. "Wireless Drive of a Piezoelectric Plate by Dipole Antenna", *IEEE Ultrasonics Symposium*, 2008; Date of Conference: Nov. 2-5, 2008, pp. 1199-1202.

Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.

DesMarais, Christina (posted on Sep. 3, 2013) "Which New Activity Tracker is Best for You?" *Health and Home, Health & Fitness , Guides & Reviews*, [Retrieved on Sep. 23, 2013 at http://www.techlicious.com/guide/which-new-activity-tracker-is-right-for-you/] 4 pp.

Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.

Fitbit User's Manual, Last Updated Oct. 22, 2009, 15 pages.

Forerunner® 201 personal trainer owner's manual, (Feb. 2006) Garmin Ltd., 48 pp.

Forerunner® 301 personal trainer owner's manual, (Feb. 2006) Garmin Ltd., 66 pp.

Forerunner® 50 with ANT+Sport™ wireless technology, Owner's Manual, (Nov. 2007) Garmin Ltd., 44 pp.

Forerunner® 205/305 Owner's Manual, GPS-enabled trainer for runners, (2006-2008), Garmin Ltd., 80 pp.

Forerunner® 405CX Owner's Manual, "GPS-Enabled Sports Watch With Wireless Sync," (Mar. 2009), Garmin Ltd., 56 pp.

Forerunner® 110 Owner's Manual, (2010) "GPS-Enabled Sport Watch," Garmin Ltd., 16 pp.

Forerunner® 210 Owner's Manual, (2010) "GPS-Enabled Sport Watch," Garmin Ltd., 28 pp.

Forerunner® 410 Owner's Manual, (Jul. 2012) "GPS-Enabled Sport Watch With Wireless Sync," Garmin Ltd., 52 pp.

Forerunner® 10 Owner's Manual (Aug. 2012), Garmin Ltd., 10 pp.

Forerunner® 310XT Owner's Manual, Multisport GPS Training Device, (2009-2013), Garmin Ltd., 56 pp.

(56) References Cited

OTHER PUBLICATIONS

Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Itagaki, Kazuya, "Key Components for Wireless Power Transmission," *Technologies & Products Press Conference*, Nov. 14, 2012. 12 pp.
Larklife, User Manual, (2012) *Lark Technologies*, 7 pp.
Lark/Larkpro, User Manual, (2012) "What's in the box," *Lark Technologies*, 7 pp.
Manivannan et al. (Mar. 2013) "Qi Open Wireless Charging Standard—A Wireless Technology for the Future," *International Journal of Engineering and Computer Science*, 2(3):573-579.
Neagle, Colin, "How wireless charging can drive near-field communications growth." *Network World*, Jan. 28, 2013, 2pp.
"Nexus 7 2nd Generation Teardown" *iFixit*, downloaded from the Internet on Aug. 4, 2014 at https://www.ifixit.com/Teardown/Nexus+7+2nd+Generation+Teardown/16072, 9 pages.
Nike+ FuelBand GPS Manual, User's Guide (Product Release Date Unknown, downloaded Jul. 22, 2013), 26 pages.
Nike+ SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
Nishigaki et al. "Piezoelectric MEMS Variable Capacitor for a UHF Band Tunable Built-in Antenna" *IEEE/MTT-S International Microwave Symposium*, Jun. 3-8, 2007, pp. 2079-2082.
"Parts of Your Band," (Product Release Date Unknown, downloaded Jul. 22, 2013) Jawbone UP Band, 1 page.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
"Wireless charging", RFID-BLOG. Downloaded Sep. 4, 2014 at http://www.rfid-blog.com?tag=wireless-charging, 2 pp.

\* cited by examiner

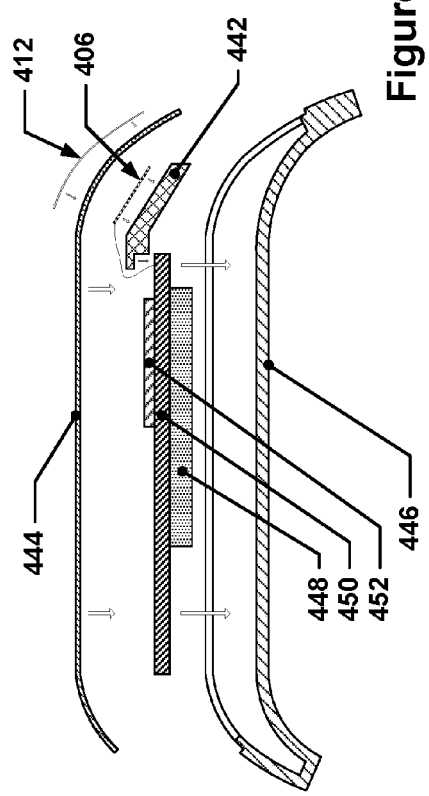
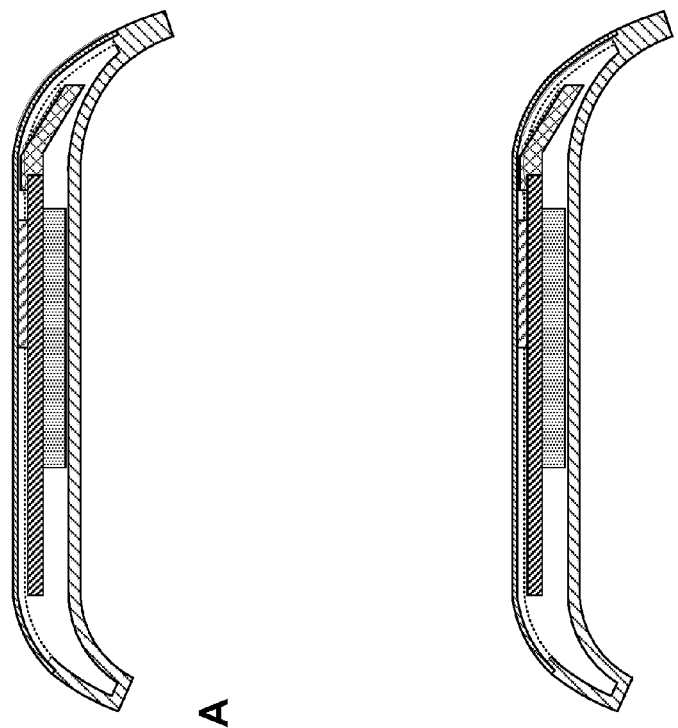
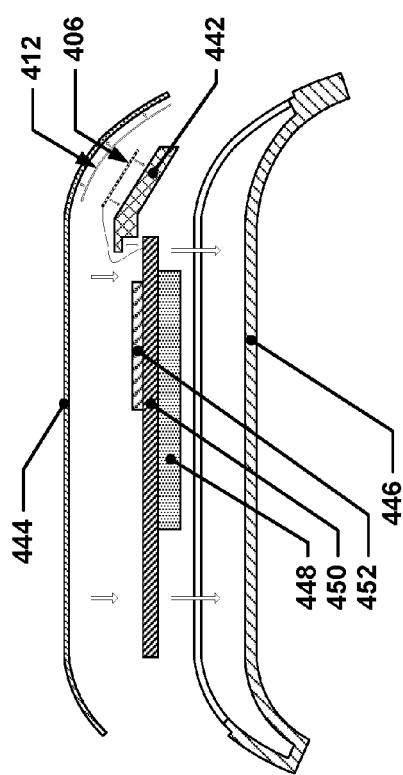
Figure 4A
Figure 4B

HYBRID PIEZOELECTRIC DEVICE / RADIO FREQUENCY ANTENNA

CROSS-REFERENCE TO RELATED APPLICATIONS

This application is a continuation of U.S. patent application Ser. No. 14/444,944, filed Jul. 28, 2014, titled "HYBRID PIEZOELECTRIC DEVICE/RADIO FREQUENCY ANTENNA," which is a continuation-in-part of U.S. patent application Ser. No. 14/290,906, filed May 29, 2014, titled "HYBRID RADIO FREQUENCY/INDUCTIVE LOOP ANTENNA," which also claims benefit of priority under 35 U.S.C. §119(e) to U.S. Provisional Patent Application No. 61/948,470, filed Mar. 5, 2014, titled "HYBRID RADIO FREQUENCY/INDUCTIVE LOOP ANTENNA," all of which are hereby incorporated by reference in their entirety.

BACKGROUND

Recent consumer interest in personal health has led to a variety of personal health monitoring devices being offered on the market. Such devices, until recently, tended to be complicated to use and were typically designed for use with one activity, e.g., bicycle trip computers.

Recent advances in sensor, electronics, and power source miniaturization have allowed the size of personal health monitoring devices, also referred to herein as "biometric tracking" or "biometric monitoring" devices, to be offered in extremely small sizes that were previously impractical. For example, the Fitbit Ultra is a biometric monitoring device that is approximately 2" long, 0.75" wide, and 0.5" deep; it has a pixelated display, battery, sensors, wireless communications capability, power source, and interface button, as well as an integrated clip for attaching the device to a pocket or other portion of clothing, packaged within this small volume.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an apparatus may be provided. The apparatus may include a ground plane, a radio-frequency radiator offset from the ground plane by at least a first distance, a feed post conductively connected to the radiator, and a piezoelectric assembly offset from the ground plane and either in conductive contact with the radiator or electrically coupled with the radiator and not in conductive contact with the radiator. The piezoelectric assembly, the radiator, the ground plane, and the feed post together may form a planar inverted-F antenna (PIFA) configured to produce and receive electro-magnetic radio-frequency signals.

In some such implementations of the apparatus, the piezoelectric assembly may include a piezoelectric material, a first electrode, and a second electrode such that the piezoelectric material is positioned between the first electrode and the second electrode and the piezoelectric assembly is configured to produce a piezoelectric effect. In some such implementations, piezoelectric material may include one or more compounds such as gallium orthophosphate, langasite, barium titanate, lead titanate, lead zirconate titanate, lithium niobate, lithium tantalate, sodium tungstate, zinc oxide, $Ba_2NaNb_5O_5$, $Pb_2KNb_5O_{15}$, sodium potassium niobate, bismuth ferrite, sodium niobate, bismuth titanate, sodium bismuth titanate, or polyvinylidene fluoride. In some further or additional implementations, the piezoelectric effect may be, for example: (a) mechanical deformation of the piezoelectric material when an electrical potential is applied across the piezoelectric material via the first and second electrodes or (b) production of an electrical potential between the first and second electrodes when mechanical stress is induced in the piezoelectric material by an external mechanical force.

In some further or additional implementations of the apparatus, the apparatus may further include a first electrical conductor and a second electrical conductor. The first electrical conductor may be connected to the first electrode and the second electrical conductor may be connected to the second electrode.

In some further or additional implementations of the apparatus, the apparatus may further include a current-blocking component such that the radiator is in conductive contact with piezoelectric assembly, the current-blocking component is configured to at least substantially block radio-frequency current from reaching the piezoelectric assembly, and the current-blocking component is in conductive contact with the feed post. In some such implementations, the current-blocking component may be located in an electrically-conductive path between the radiator and the piezoelectric assembly.

In some further or additional implementations of the apparatus, the piezoelectric assembly may at least partially overlap the ground plane.

In some further or additional implementations of the apparatus, the radiator may overlap less than all of the piezoelectric assembly.

In some further or additional implementations of the apparatus, the radiator may overlap all of the piezoelectric assembly.

In some further or additional implementations of the apparatus, the piezoelectric assembly may be separated from the radiator by a first gap and the piezoelectric assembly may be electrically coupled with the radiator and not in conductive contact with the radiator. In some such implementations, the apparatus may further include an insulating layer that is interposed between the radiator and the piezoelectric assembly in the first gap. In some such implementations the ground plane may be provided by a structure located on an opposite side of the first housing portion from the radiator. In some such implementations, the structure may be selected from the group consisting of a printed circuit board, a flexible circuit board, a metal plate contained within the apparatus, and a metal plate at least partially providing an exterior surface of the apparatus. In some further or additional implementations, the apparatus may further include a first housing portion and a second housing portion such that the radiator may be supported by the first housing portion, the piezoelectric assembly may be supported by the second housing portion, and the first housing portion may be mated to the second housing portion such that the piezoelectric assembly and the radiator are separated by the first gap.

In some further or additional implementations, the apparatus my further include a plastic carrier and a substrate with a printed circuit such that the radiator may be supported by the plastic carrier, the plastic carrier may be supported by the substrate with the printed circuit, the substrate with the printed circuit may act as the ground plane, and the piezoelectric assembly may also be supported by the plastic carrier. In some further or additional implementations, the apparatus may further include a housing having a first surface and a second surface such that the first surface and the second surface may nominally be on opposing sides of a portion of the housing and define the first gap, the radiator may be formed by a metallization layer deposited on the first surface, and the piezoelectric assembly may be located on or adjacent to the second surface such that the second surface is interposed between the first surface and the piezoelectric assembly. In some further or additional implementations, the apparatus may further include a housing having a first surface and a second surface, such that the first surface and the second surface may nominally be on opposing sides of a portion of the housing and define the first gap, the radiator may be formed by a metallization layer deposited on the second surface, and the piezoelectric assembly may be located on or adjacent to the second surface such that the radiator is interposed between the second surface and the piezoelectric assembly.

In some further or additional implementations of the apparatus, the first gap may be less than or equal to 2 mm.

In some further or additional implementations of the apparatus, the piezoelectric assembly may be substantially circular. In some such implementations, the radiator may be substantially circular in overall shape such that the radiator has an average diameter of between 5 mm and 25 mm and the piezoelectric assembly has an average diameter of between 5 mm and 25 mm.

In some further or additional implementations of the apparatus, the piezoelectric assembly may be substantially rectangular in overall shape.

In some further or additional implementations of the apparatus, the radiator may be substantially circular in overall shape.

In some further or additional implementations of the apparatus, the radiator may be O-shaped.

In some further or additional implementations of the apparatus, the radiator may be C-shaped.

In some further or additional implementations of the apparatus, the radiator may be L-shaped, U-shaped, or rectangular-shaped.

In some further or additional implementations of the apparatus, the radiator may be a solid plate.

In some further or additional implementations of the apparatus, the first distance may be between about 0.5 mm and 10 mm.

In some further or additional implementations of the apparatus, the ground plane may be a non-planar surface.

In some further or additional implementations of the apparatus, the radiator and the piezoelectric assembly may be in electrically-conductive contact with one another.

In some further or additional implementations of the apparatus, the apparatus may further include a shorting post conductively connecting the radiator to the ground plane such that the piezoelectric assembly, the radiator, the ground plane, the shorting post, and the feed post form a planar inverted-F antenna (PIFA) configured to produce and receive electric radio-frequency signals in a Bluetooth-compatible frequency band.

In some further or additional implementations of the apparatus, the apparatus may further include a shorting post conductively connecting the radiator to the ground plane such that the piezoelectric assembly, the radiator, the ground plane, the shorting post, and the feed post form a planar inverted-F antenna (PIFA) configured to produce and receive electric radio-frequency signals in a GPS-compatible frequency band.

In some further or additional implementations of the apparatus, the radiator, the ground plane, and the piezoelectric assembly may be located on a common, non-recurvate reference surface.

In some further or additional implementations of the apparatus, the piezoelectric assembly may be configured to produce a sound. In some such implementations, the piezoelectric assembly may be configured to produce a sound when the piezoelectric assembly is powered. In some further or additional such implementations, the piezoelectric assembly may be configured to produce a range of sounds.

In some further or additional implementations of the apparatus, the piezoelectric assembly is configured to produce a beep or a series of beeps.

In some further or additional implementations of the apparatus, the apparatus may further include a battery and the piezoelectric assembly may be configured to scavenge energy by converting vibrations induced in the piezoelectric assembly into an electrical charge and output the electrical charge to the battery.

In some implementations, a method may be provided. The method may include: a) providing a radio-frequency radiator, b) mounting the radiator to a first surface of a first housing component, c) providing a piezoelectric assembly, and d) placing the piezoelectric assembly such that the piezoelectric assembly is electrically coupled with the radiator.

In some such implementations of the method, the piezoelectric assembly may be bonded to the first surface and the radiator is interposed between the piezoelectric assembly and the first surface.

In some further or additional implementations of the method, the method may further include: providing a second housing component, bonding the piezoelectric assembly to a second surface of the second housing component, and mating the second housing component to the first housing component. The piezoelectric assembly may be bonded to the second surface in a location that causes (d) to be concurrently performed when the second housing component is mated to the first housing component.

In some further or additional implementations of the method, the first surface and the second surface may be offset from one another in directions normal to the first surface and intersecting the radiator when the first housing component and the second housing component are mated together.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals may refer to similar elements.

FIG. 4A depicts a schematic side view (left) and side exploded view (right) of one configuration of an example device housing and hybrid piezoelectric device/RF antenna.

FIG. 4B depicts a schematic side view (left) and side exploded view (right) of one configuration of another example device housing and hybrid piezoelectric device/RF antenna.

DETAILED DESCRIPTION

Figure 1A:
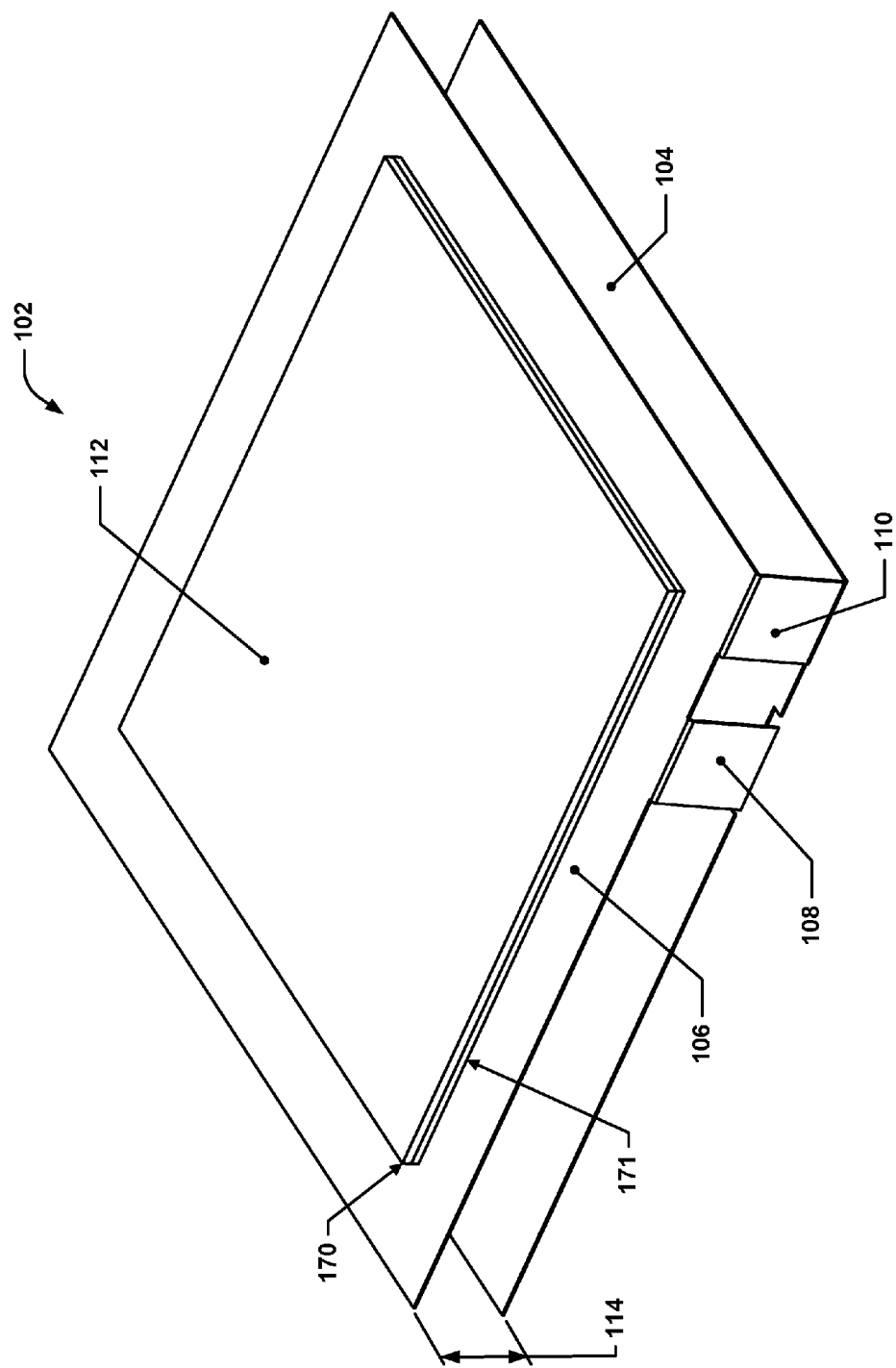
FIG. 1A depicts an example of a hybrid piezoelectric device/radio-frequency (RF) antenna.

Modern electronic devices frequently include one or more radio-frequency antennas to facilitate wireless communication with other electronic devices. Such an antenna is typically designed to be particularly receptive to (or emissive of) radio frequency energy at frequencies within the frequency band for the wireless communications protocol that the antenna is designed to support, and, ideally, much less receptive to (or emissive of) radio frequency energy at frequencies outside of the frequency band. Antennas may achieve such selectivity by virtue of their physical geometry and the dimensions that define that geometry. Antennas for different communications protocols are typically kept separated from one another within a device to prevent the antennas from interfering with one another.

Additionally, modern electric devices frequently utilize piezoelectric assemblies to, for example, produce sounds to communicate with users of the devices. Piezoelectric speakers are often used to produce single frequency sounds such as beeps. However, other implementations of piezoelectric speakers may product sounds in multiple frequencies, allowing piezoelectric speakers to be used in the same manner as traditional loudspeakers.

Piezoelectric assemblies may also have additional applications in modern electric devices. For example, piezoelectric assemblies may be utilized as energy scavenging devices. In such an implementation, a piezoelectric assembly within an electronic device may scavenge electric power through the electric charge generated by the piezoelectric assembly when the piezoelectric assembly is subjected to vibrations produced by movement of the wearer. Also future piezoelectric assemblies may be used to produce vibrations detectable by touch, allowing the electric device to communicate information to the user through haptic feedback.

Disclosed herein are several hybrid RF/piezoelectric structures that provide both for piezoelectric functionality, e.g., producing sounds or scavenging energy, as well as RF operations, e.g., communications over an RF signal band. In each such implementation, a piezoelectric assembly may be placed in close proximity to (or be in conductive contact with) the radiator for an inverted-F antenna (IFA) (or other antenna structure) of an electronic device. The RF radiator may be used as an electrode of the piezoelectric assembly or the RF radiator may be placed sufficiently close to the piezoelectric assembly such that the RF radiator may power the piezoelectric assembly through mutual coupling. The radiator and piezoelectric assembly may be placed sufficiently close enough together that there is sufficient electrical coupling between the piezoelectric assembly and the radiator to cause the piezoelectric assembly or an electrode of the piezoelectric assembly to act as, in effect, a large planar or curvilinear surface element of the antenna that the radiator is part of. At the same time, the piezoelectric assembly may still be capable of other functions involving the piezoelectric effect, e.g., producing sounds or scavenging energy. By combining the piezoelectric assembly with the radiator of an RF antenna, RF functionality and piezoelectric functionality may be combined into a smaller volume while still providing good performance in the RF regime as well as for piezoelectric functions.

FIG. 1A depicts an example of a hybrid piezoelectric device/radio-frequency (RF) antenna. In FIG. 1A, a hybrid antenna 102 is shown. The hybrid antenna 102 includes a ground plane 104, a RF radiator 106, a feed post 108, a shorting post 110, and a piezoelectric assembly 112. The RF radiator 106, in this example, is offset from the ground plane 104 by a first distance 114. The RF radiator 106 and the ground plane 104, when combined with the feed post 108 and the shorting post 110, form an inverted-F antenna-like structure. In some implementations, the first distance 114 may be between about 0.5 mm and 10 mm or, in some further implementations, between about 2 mm to 5 mm.

The piezoelectric assembly 112 may include a first piezoelectric electrode 170 and a piezoelectric material 171. The piezoelectric material in the implementation in FIG. 1A and in other implementations described in this disclosure may be a material that exhibits piezoelectric properties, including gallium orthophosphate, langasite, barium titanate, lead titanate, lead zirconate titanate, lithium niobate, lithium tantalate, sodium tungstate, zinc oxide, $Ba_2NaNb_5O_5$, $Pb_2KNb_5O_{15}$, sodium potassium niobate, bismuth ferrite, sodium niobate, bismuth titanate, sodium bismuth titanate, and polyvinylidene fluoride. The piezoelectric material 171 shown in FIG. 1A is a flat plate that is rectangular in shape. However, in other implementations, the piezoelectric material may be in a variety of other shapes including circular, triangular, polygonal, etc. Indeed, the piezoelectric material may be in multiple different three-dimensional shapes including cubes, pyramids, spheres, lens, dishes, domes, complex multi-planar shapes, and other shapes.

The piezoelectric assembly may be used for any function suitable for a piezoelectric device. For example, the piezoelectric assembly may be used to produce sounds. The piezoelectric assembly may produce sounds in a single pitch, such as tones used for a beep or a series or combination of beeps, or may produce sounds in many different pitches, thus allowing the piezoelectric assembly to, for example, play audio clips or music. The sounds produced by the piezoelectric assembly may be another way for an electronic device to interact with the user. Such interaction may be in addition to haptic feedback produced by the electronic device. One example of a situation where sounds from the piezoelectric assembly may be useful would be in situations where a user of the electronic device may not notice haptic feedback, such as during activities with lots of user movement, for example, running or biking. In such a situation, the user may notice a sound produced by the electronic device.

In addition, the piezoelectric assembly may be used for energy scavenging. Battery life is often an important concern in electronic devices. Piezoelectric assemblies may convert mechanical force, such as the force felt from vibrations, into electrical energy. In such a way, vibrations from, for example, the steps of the user, may be converted into electrical energy. Energy scavenging by the piezoelectric assembly may be a way to extend the battery life of the electronic device that the hybrid antenna is integrated into.

In this implementation, the RF radiator 106 may also function as a piezoelectric electrode. Other implementations may include a second piezoelectric electrode separate from the RF radiator. The piezoelectric electrodes, which in FIG. 1A include the RF radiator 106, are in electrically-conductive contact with the piezoelectric material 171. The piezoelectric electrodes may distribute an electrical charge or electrical charges across the piezoelectric material 171. In certain implementations, an electrical charge may be applied to the piezoelectric material 171 via the first piezoelectric electrode 170 from an electrical conductor in electrically-conductive contact with the first piezoelectric electrode. Other implementations may apply an electrical charge through the second piezoelectric electrode, whether the second piezoelectric electrode is the RF radiator or a separate second piezoelectric electrode.

As shown, the RF radiator 106 is a rectangular plate. However, in other implementations, the RF radiator 106 may take the form of a variety of other shapes. Some additional possible shapes for the RF radiator are described in detail further in this application, including, but not limited to, those shown and described with reference to FIGS. 5A, 5B, 5C, 6A, 6B, 6C, and 6D.

The shorting post 110 may provide for electrically-conductive contact between the ground plane 104 and the RF radiator 106. While shown as a single, continuous structure, the shorting post 110 may be provided by a number of structures, e.g., a bonded wire, a sprung contact pin, a combination of such features, or other features that provide for electrically-conductive contact.

The feed post 108 provides an electrically conductive path for receiving or sending electrical signals generated by the hybrid antenna 102 in response to received RF radiation or produced in the hybrid antenna 102 in response to such electrical signals. The feed post 108 may also be provided by structures other than the single, continuous structure shown, e.g., by a bonded wire, a sprung contact pin, a combination of such features, or other features that provide for electrically-conductive contact with the RF radiator 106.

Figure 1B:
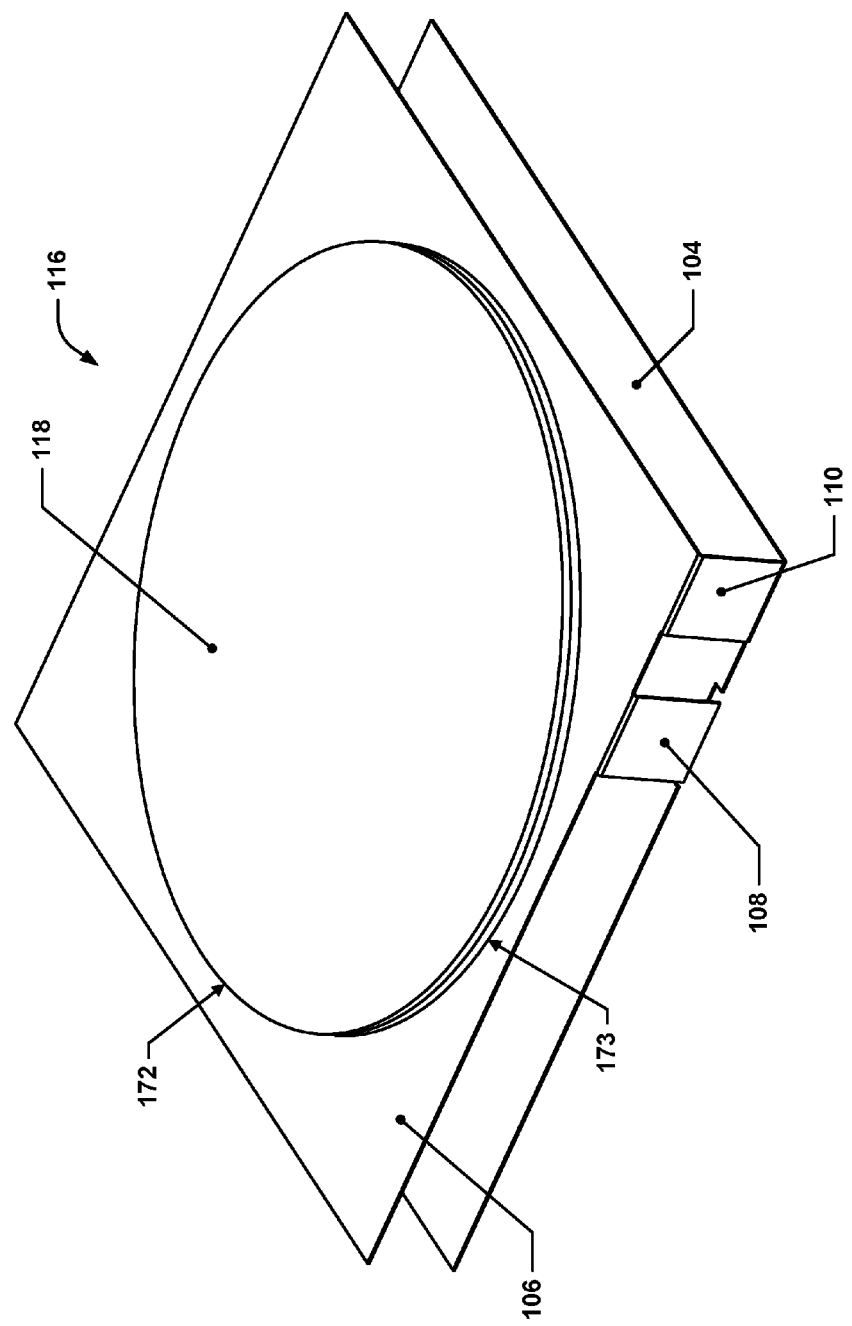
FIG. 1B depicts another example of a hybrid piezoelectric device/RF antenna.

FIG. 1B depicts another example of a hybrid piezoelectric device/RF antenna. A hybrid antenna 116 is shown in FIG. 1B and includes a ground plane 104, a RF radiator 106, a feed post 108, a shorting post 110, and a piezoelectric assembly 118. The ground plane 104, the RF radiator 106, the feed post 108, and the shorting post 110 in FIG. 1B are similar in configuration to their respective components in FIG. 1A.

The piezoelectric assembly 118 in FIG. 1B includes a first piezoelectric electrode 172 and a piezoelectric material 173. One way in which the first piezoelectric electrode 172 and the piezoelectric material 173 differ from their respective components in FIG. 1A is that the first piezoelectric electrode 172 and the piezoelectric material 173 are circular discs rather than rectangular in shape. Certain implementations of the hybrid antenna may utilize commercial-off-the-shelf (COTS) piezoelectric assemblies. Many COTS piezoelectric assemblies are available in circular forms, so it may be advantageous to produce a hybrid antenna utilizing these circular COTS piezoelectric assemblies.

In FIG. 1B, the ground plane 104 and the RF radiator 106 are rectangular in shape, but in other implementations, the ground plane and/or the RF radiator may be in other shapes such as a substantially circular shape substantially matching the shape of the piezoelectric assembly 118. Additionally, the RF radiator 106 in the implementation shown in FIG. 1B also functions as a piezoelectric electrode. In other implementations, especially in implementations utilizing COTS piezoelectric assemblies, the piezoelectric assembly may have a second piezoelectric electrode positioned opposite of the first piezoelectric electrode 172. In such an implementation, the RF radiator may be in conductive contact with the second piezoelectric electrode or the second piezoelectric electrode and the RF radiator may be separated by a gap. Implementations where the second piezoelectric electrode and the RF radiator are separated by a gap are described in detail further in this application, including in the description for FIGS. 1C and 1E.

Figure 1C:
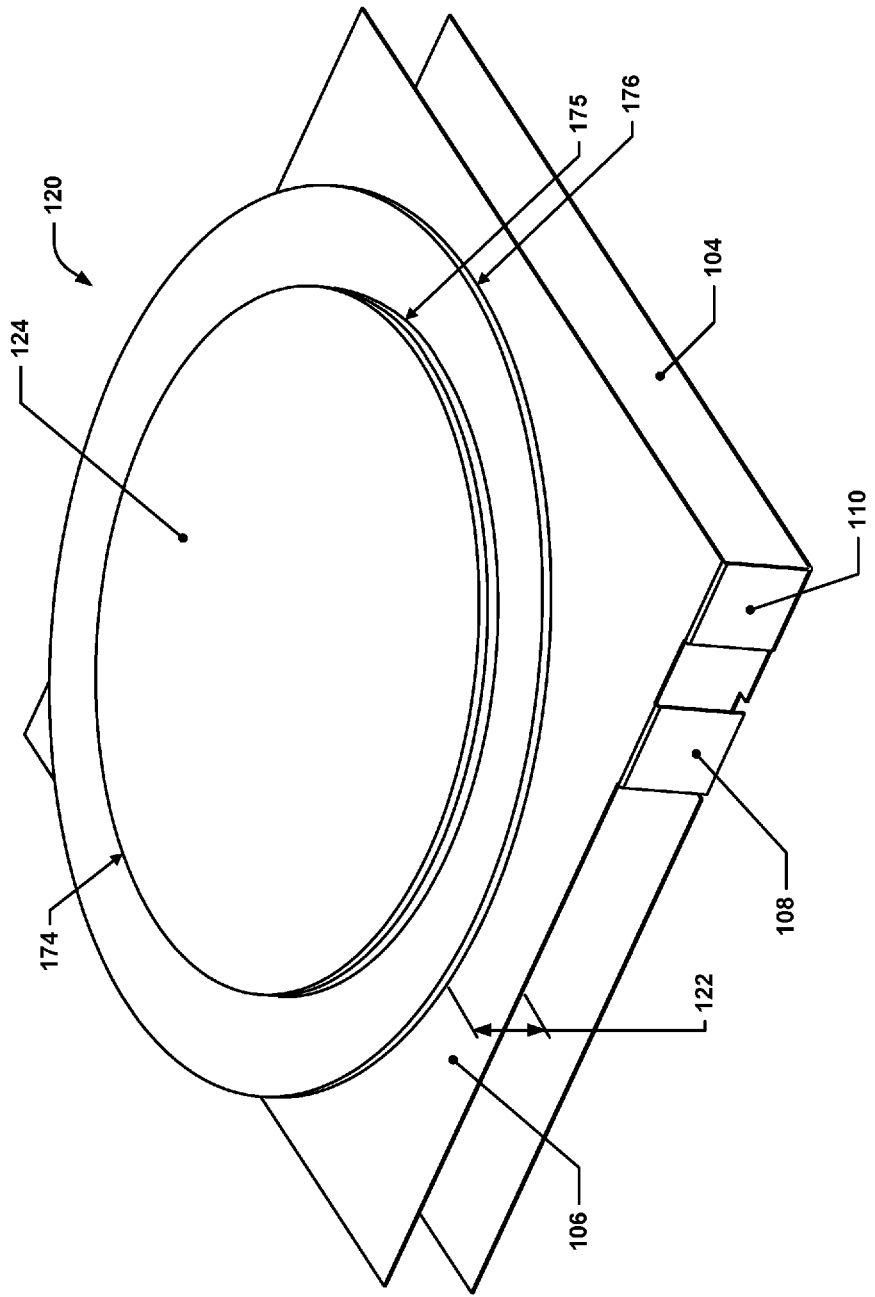
FIG. 1C depicts an example hybrid piezoelectric device/RF antenna with an offset piezoelectric assembly.

FIG. 1C depicts an example hybrid piezoelectric device/ RF antenna with an offset piezoelectric assembly. A hybrid antenna 120 is shown in FIG. 1C and includes a ground plane 104, a RF radiator 106, a feed post 108, a shorting post 110, and a piezoelectric assembly 124. The ground plane 104, the RF radiator 106, the feed post 108, and the shorting post 110 in FIG. 1C are similar in configuration to their respective components in FIG. 1A.

A difference between the hybrid antenna implementation in FIG. 1A and the hybrid antenna implementation in FIG. 1C is that the piezoelectric assembly 124 in FIG. 1C is offset from the RF radiator 106 by a first gap 122 instead of resting on the RF radiator. The first gap 122 may be an air gap (as shown) or it may be filled with a generally non-conductive material, e.g., plastic, material, composite, polyurethane foam, double-sided adhesive tape, etc. In the implementation shown in FIG. 1C, the piezoelectric material 175 may receive an electrical charge through electrical conductors attached to the piezoelectric electrodes 174 and 176. The electrical conductors are not shown in FIG. 1A. In other implementations, the piezoelectric material may not be in electrically conductive contact with a power source. Instead, the piezoelectric material may inductively coupled with a power source such as the RF radiator 106. In such an implementation, the piezoelectric assembly may not include the piezoelectric electrodes.

In some implementations, the first gap 122 may be filled or partially filled by an insulating material. An implementation with an insulating material filling the first gap 122 is described in greater detail in FIG. 1E. In some implementations, the first gap 122 may be less than or equal to 10 mm and, in some implementations, may be less than or equal to 8 mm, 6 mm, 4 mm, or 2 mm. In some particular implementations, the first gap 122 may be less than about 2 mm.

Figure 1D:
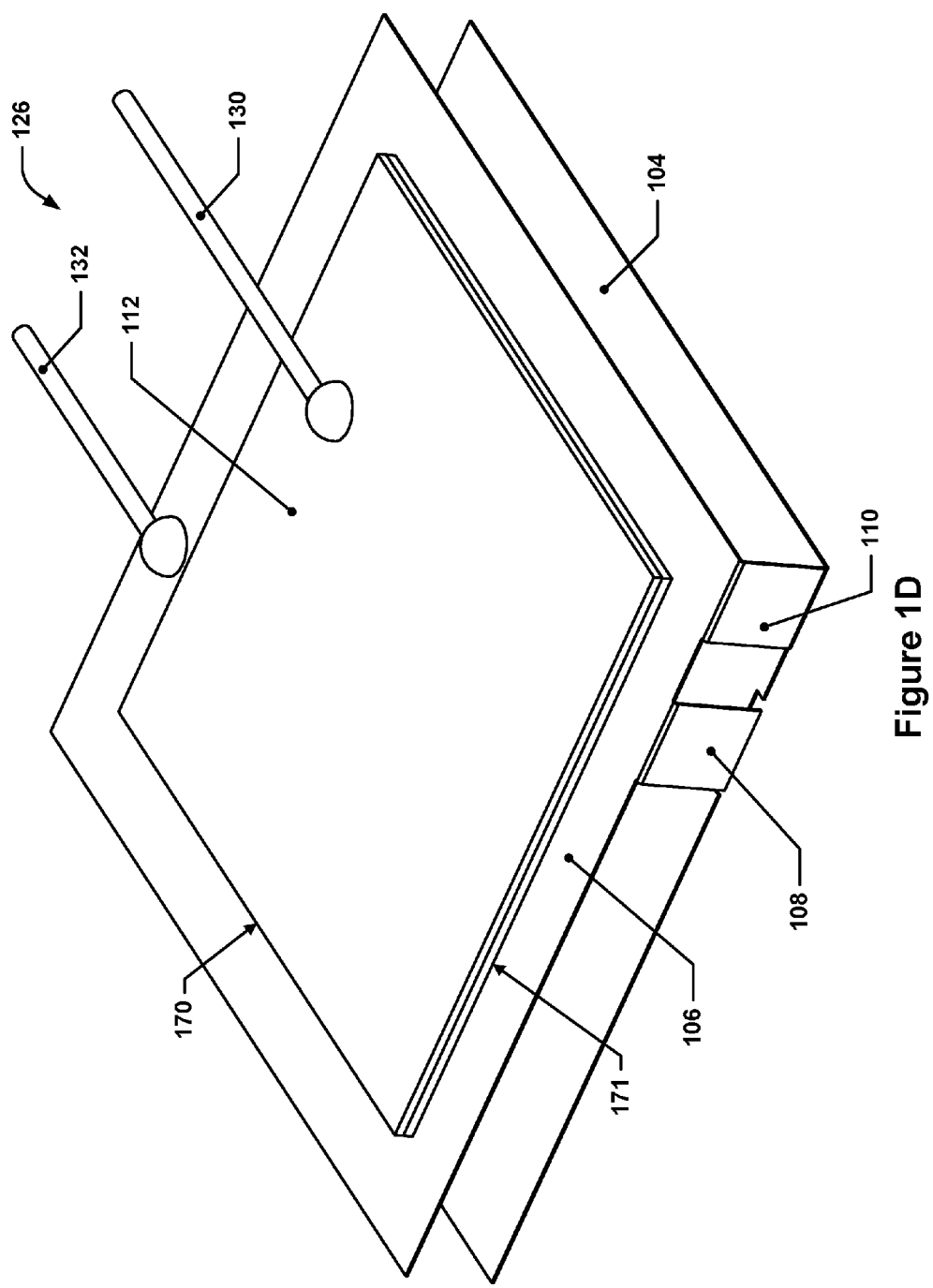
FIG. 1D depicts an example hybrid piezoelectric device/RF antenna with electrical conductors.

FIG. 1D depicts an example hybrid piezoelectric device/RF antenna with electrical conductors. A hybrid antenna 126 shown in FIG. 1D. The hybrid antenna 126 is similar in configuration to the hybrid antenna 102 shown in FIG. 1A. However, the implementation of the hybrid antenna 126 shown in FIG. 1D further includes a first electrical conductor 130 and a second electrical conductor 132.

The first electrical conductor 130 may be attached to the first piezoelectric electrode 170. The second electric conductor 132 may be attached to the RF radiator 106 as the RF radiator 106 in the implementation of the hybrid antenna 126 shown in FIG. 1D also functions as a piezoelectric electrode. In the depicted implementation, the first and second conductors are depicted as being soldered onto their respective piezoelectric device electrodes, although, in practice, such connections may be made by any form of electrically conductive interface. For example, in some implementations, one or both such connections may be made using spring contacts, e.g., a conductive leaf spring that engages with an electrode. This may allow, for example, for easy electrical connection to COTS piezoelectric devices. The first electrical conductor 130 and the second electrical conductor 132 may be attached to a power source not shown in FIG. 1D.

In certain implementations, the feed post 108 and/or the shorting post 110 may be a sprung contact or other type of electrical connections. Such configurations may be especially useful when utilizing off-the-shelf piezoelectric devices that do not include feed posts or shorting posts. In such implementations, the sprung contact, e.g., a feed post that terminates in a leaf spring that presses against a bottom electrode of a piezoelectric device, may provide power to (or receive power from) the piezoelectric device via that sprung contact while also allowing RF signals to reach the bottom electrode (which may, for RF purposes, act as a plate radiator of a PIFA). This may facilitate implementations where only the first electrical conductor 130 may be used. In such implementations, the RF radiator may be used as a second electrical conductor for the piezoelectric assembly 112.

An electrical charge may be applied through either the first electrical conductor 130 or the second electrical conductor 132 to excite the piezoelectric assembly 112. In the implementation in FIG. 1D, the first piezoelectric electrode 170 and the RF radiator 106 function to distribute the electrical charge across the top and bottom surfaces, respectively, of the piezoelectric material 171. When the electrical charge is applied, the piezoelectric material 171 mechanically deforms. When an alternating current (AC) is applied to the piezoelectric material 171, the piezoelectric material 171 vibrates. The piezoelectric material 171 may vibrate at frequencies that are audible to the human ear. If the hybrid antenna 126 is incorporated into an electronic device, the sounds created by the piezoelectric material 171 may be used to communicate information to a wearer or user.

Additionally or alternatively, the piezoelectric material 171 may generate electrical voltage, such as AC voltage, when subjected to vibrations. The source of the vibrations may be from motions experienced by a worn electronic device, such as vibrations from the footsteps, arm motions, or other motions of the wearer. The electrical voltage generated by the piezoelectric material 171 may be transmitted by the first electrical conductor 130 or the second electrical conductor 132 to power a rechargeable battery, capacitor, or capattery located elsewhere in the electric device.

Figure 1E:
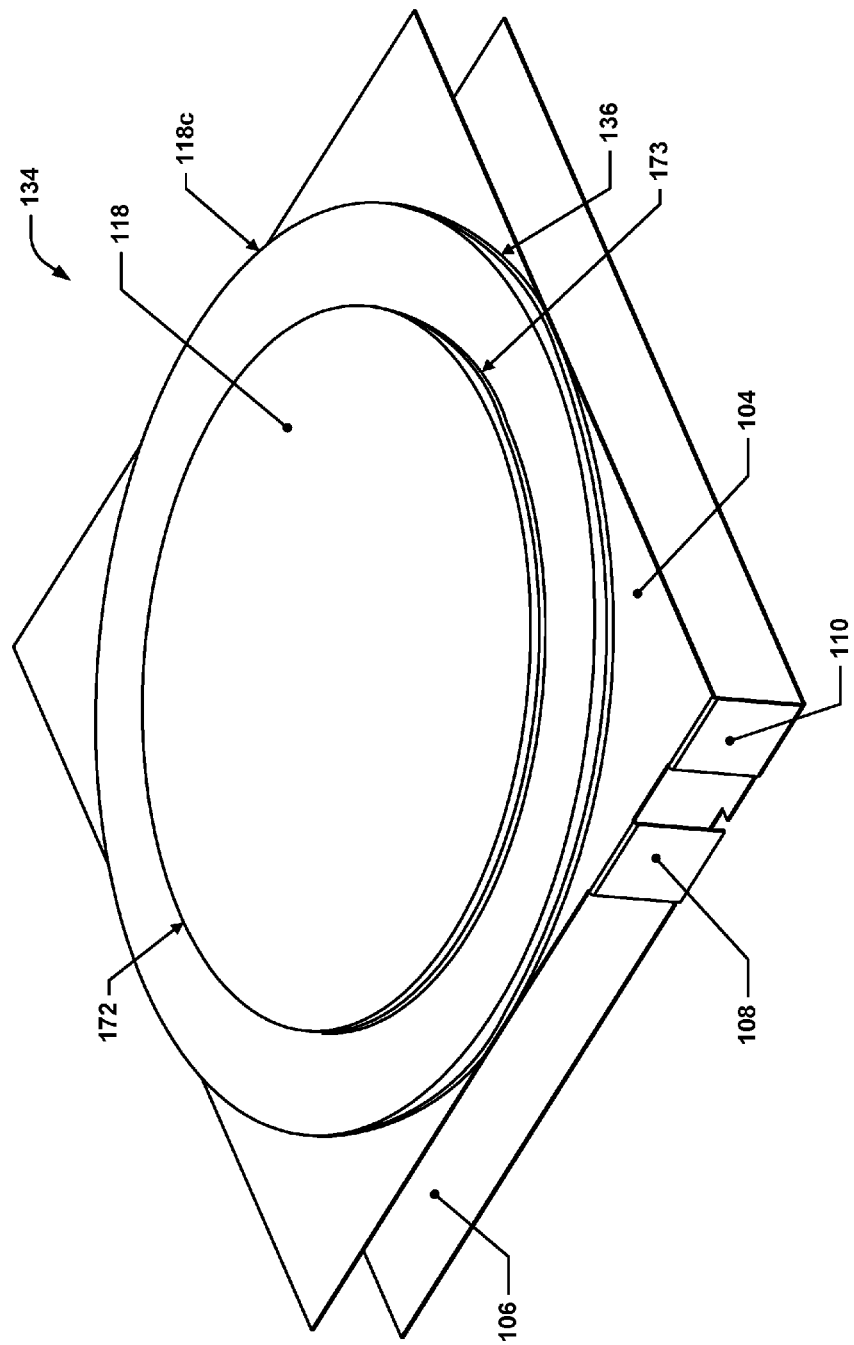
FIG. 1E depicts an example hybrid piezoelectric device/RF antenna with an insulated piezoelectric assembly.

FIG. 1E depicts an example hybrid piezoelectric device/RF antenna with an insulated piezoelectric assembly. A hybrid antenna 134 is shown in FIG. 1E. The hybrid antenna 134 is similar in configuration to the hybrid antenna 120 shown in FIG. 1C. However, the implementation of the hybrid antenna 134 shown in FIG. 1E further includes an insulating layer 136 located between the RF radiator 104 and the second piezoelectric electrode 118c.

The insulating layer 136 may be insulation selected from a variety of different materials. The piezoelectric assembly 118 of the implementation shown in FIG. 1E may be powered through mutual coupling or it may be powered through electrical charges provided by a power source that is electrically conductively coupled with the piezoelectric assembly 118. If the piezoelectric assembly 118 is powered through mutual coupling, it may be inductively coupled with the RF radiator 104 or be inductively coupled with another source not shown in FIG. 1E. In cases where the piezoelectric assembly and the RF radiator are inductively coupled, such materials should generally be selected so as to not interfere unduly with inductive coupling between the RF radiator and the piezoelectric assembly.

FIGS. 1C and 1E both depict hybrid antennas in which the piezoelectric assembly is inductively coupled with the RF radiator, i.e., no conductive contact is needed between the RF radiator and the piezoelectric assembly. This facilitates the use of COTS components as COTS piezoelectric assemblies often include two electrodes sandwiching a piezoelectric material. A COTS piezoelectric assembly of such a configuration may be overlaid on an RF radiator without requiring any modification of the piezoelectric assembly. However, in some implementations, the piezoelectric assembly and RF radiator of a hybrid antenna may be conductively coupled. Such conductive contact may be provided, for example, by way of a lead that is attached to both the RF radiator and the piezoelectric assembly, or may be provided by a more integrated solution, such as a circuit traces on a common substrate that include both material for the RF radiator and the piezoelectric assembly.

Figure 2:
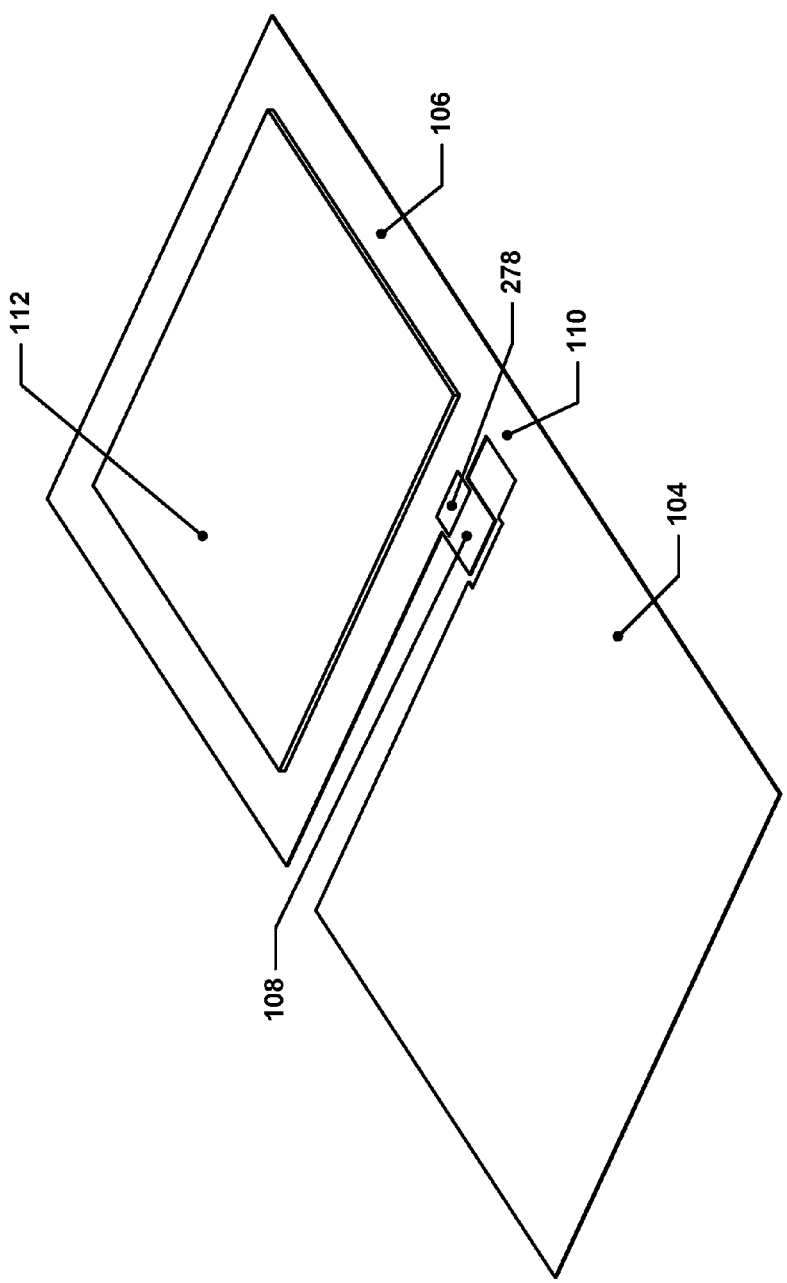
FIG. 2 depicts the example hybrid piezoelectric device/RF antenna of FIG. 1A unfolded into a flat configuration.

FIG. 2 depicts the example hybrid piezoelectric device/RF antenna of FIG. 1A unfolded into a flat configuration. A hybrid antenna 238 is shown. The hybrid antenna 238 includes a ground plane 104, a shorting post 110, a feed post 108, a RF radiator 106, and a piezoelectric assembly 112.

It is to be understood that either the "folded" version of the hybrid antenna 102 shown in FIG. 1A or the "flat" version of the hybrid antenna 238 may be used to provide combined RF and piezoelectric capabilities in a common package. It is also to be understood that, in addition to the components shown, some form of direct-current-blocking, e.g., a capacitor or series capacitor, may be provided to isolate the piezoelectric assembly and operation from the RF circuitry and operation. The current-blocking components may be placed on any portion of the hybrid antenna, including on any shorting posts and feed posts. In certain implementations, the current-blocking components such as current blocking component 278 shown in FIG. 2, may be placed upstream of the point where the feed post 108 transitions to the RF radiator 106 as shown in FIG. 1A.

"Folded" versions of hybrid antennas may be referred to herein as "recurvate," whereas "flat" versions of hybrid antennas may be referred to herein as "non-recurvate" since the "flat" version does not fold back over itself. Any of the hybrid antennas disclosed herein may be provided in both recurvate and non-recurvate configurations.

As suggested by FIG. 2, it is not necessary for the ground plane to be directly "underneath" the RF radiator, as was shown by FIGS. 1A through 1E. The ground plane may be provided in a number of different locations, and by a number of different structures, that are located in the vicinity of the RF radiator and the piezoelectric assembly. For example, the ground plane may be provided by a large metalized area, e.g., such as is shown in FIG. 2; the conductive traces in a printed circuit board (PCB) or flexible circuit board (FCB); a metal plate or surface within the housing of a device that contains the hybrid antenna; a metal plate or surface that forms the exterior of such a housing; etc.

Figure 3A:
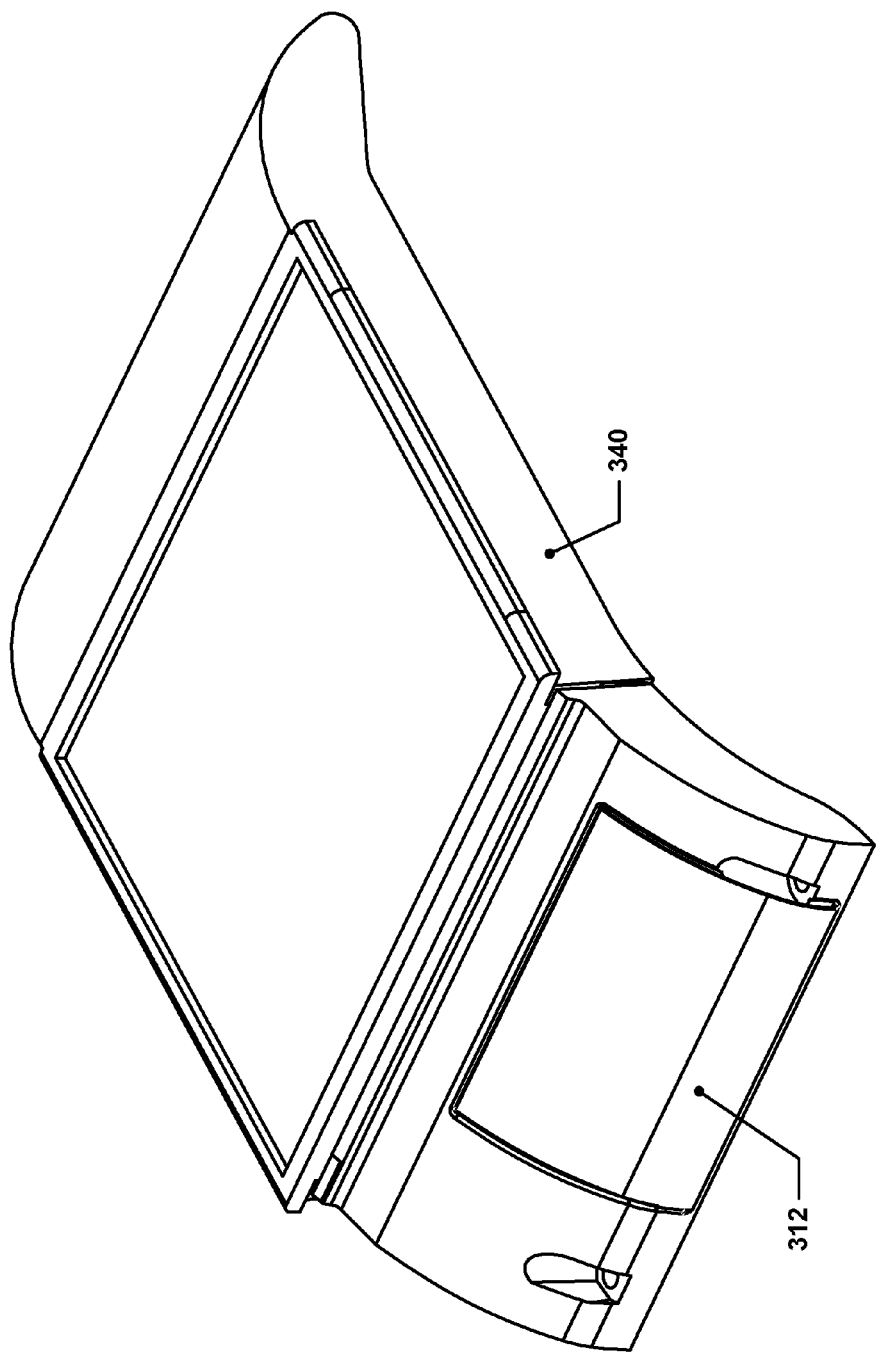
FIG. 3A depicts an example device housing that includes an example hybrid piezoelectric device/RF antenna.
Figure 3B:
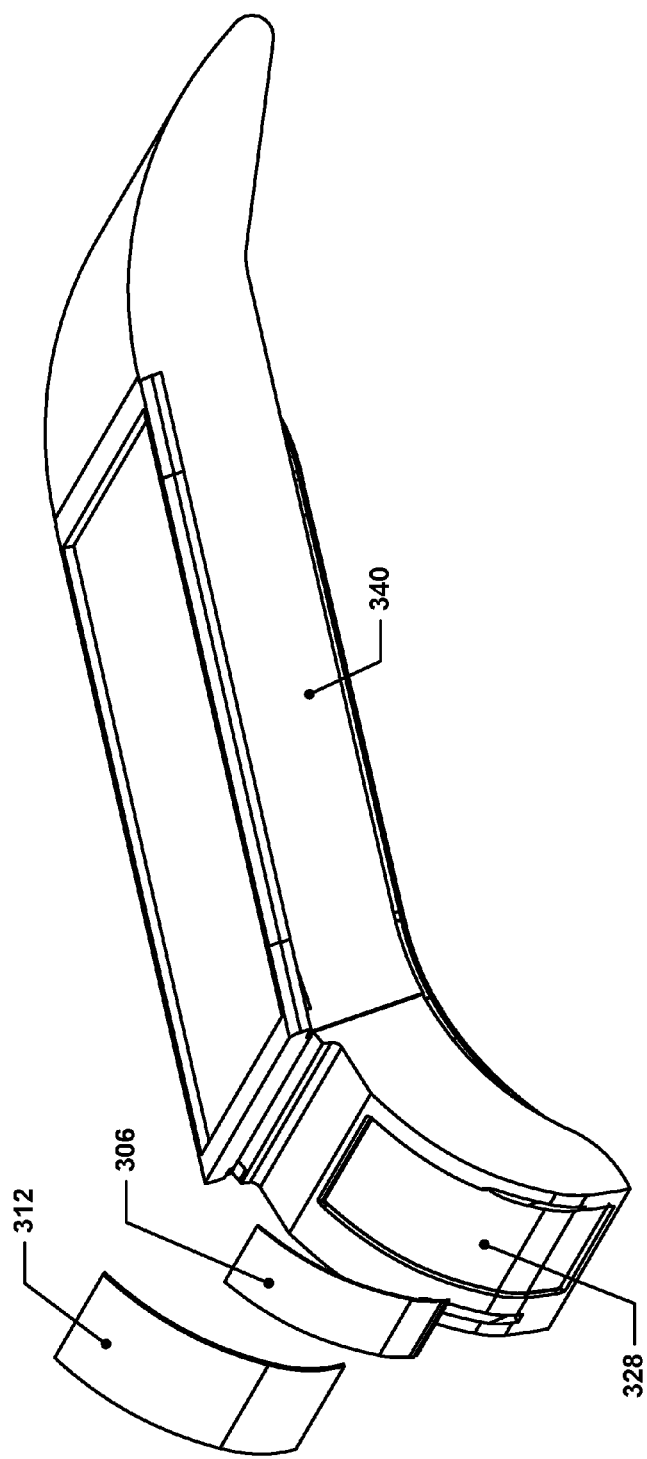
FIG. 3B depicts an exploded view of the example device housing that includes the example hybrid piezoelectric device/RF antenna of FIG. 3A.

FIG. 3A depicts an example device housing that includes an example hybrid piezoelectric device/RF antenna. FIG. 3B depicts an exploded view of the example device housing and the example hybrid piezoelectric device/RF antenna of FIG. 3A. FIGS. 3A and 3B provide an example of a hybrid antenna implementation that demonstrates the flexibility of such antennas in terms of packaging.

The example device in FIGS. 3A and 3B include a housing 340, a piezoelectric assembly 312, a recess 328, and a RF radiator 306. The RF radiator 306 is not shown in FIG. 3A as it is underneath the piezoelectric assembly 312, but it is shown in FIG. 3B. The recess 328 is shown in better detail in FIG. 3B and so is specifically called out in FIG. 3A.

The housing 340 may be designed to accommodate a display that will be worn on a person's wrist. A wristband (not shown) may be connected to the opposing ends of the housing, and the completed unit may be worn on someone's wrist. The down-turned ends of the housing 340 may allow the housing to conform better to the cross-sectional curvature of a person's forearm. The bulk of the interior of the housing (accessible via the underside of the housing, for example, may be occupied by various electrical components, including a PCB or FCB that includes, for example, various sensors, processors, power management components, etc. The opposing, curved ends of the housing may be designed to be inserted into complementary recesses in matched pairs of wristband straps. The convex surfaces of the curved ends of the housing may provide a useful surface upon which to mount or deposit an RF radiator, e.g., such as RF radiator 306 (shown in FIG. 3B). The RF radiator 306 may, for example, be deposited directly onto the housing 340 via, for example, laser direct structuring (LDS), or may be provided, for example, as a stamped foil or thin sheet metal part that is adhered, clipped, or otherwise attached to the housing 340.

A piezoelectric assembly 312 may then be placed over the RF radiator 306 such that there is electrically conductive contact or inductive coupling between the two components. The piezoelectric assembly 312 may be assembled in a variety of ways. For example, a COTS piezoelectric assembly may be adhesively assembled to the RF radiator through a self-adhesive sticker or glue. If desired, a recess 328 may be provided on the housing 340 to allow the piezoelectric assembly 312 and RF radiator 306 to be recessed from the nominal surface of the housing on which they are mounted. This may allow a mating component, e.g., a wristband strap, to be mated to the housing 340 where the hybrid antenna is located without introducing a high risk of accidentally dislocating the piezoelectric assembly 312 during such installation. A PCB (not shown in FIGS. 3A and 3B, but shown in FIGS. 4A-4E) may extend into the curved region of the housing underneath the RF radiator 306 and serve as a ground plane for the hybrid antenna formed by the RF radiator 306 and the piezoelectric assembly 312. Although not shown in FIGS. 3A and 3B, there may be a feed-through via or vias in the housing 340 to accommodate some form of shorting post and some form of feed post (also not shown). Such vias may allow RF components located within the housing 340, e.g., on the aforementioned PCB, to be in conductive electrical contact with the RF radiator 306. These vias may, for example, both be located near one end of the RF radiator 306 or may be located near other parts of the hybrid antenna.

As is at least partially evident from FIGS. 3A and 3B, it is not necessary for the RF radiator, the piezoelectric assembly, or the ground plane to be flat. These structures may be somewhat curved or non-planar and still provide effective RF and piezoelectric capabilities. Furthermore, it is not necessary that the RF radiator and/or the piezoelectric assembly be parallel to the ground plane—while there should be some separation distance between the RF radiator/piezoelectric assembly and the ground plane, this separation distance may vary over the length and width of the RF radiator or the length and width of the piezoelectric assembly. For example, the RF radiator and the piezoelectric assembly may both be made to conform to a curved surface, as is shown in FIGS. 3A and 3B, but the ground plane may be provided by a relatively flat PCB.

The various implementations discussed above may be used, for example, to provide a hybrid antenna that provides both Bluetooth functionality and piezoelectric functionality. Such dual-functionality may be of particular use in highly-integrated devices having an extremely small form factor. For example, the assignee of the present application produces personal biometric monitoring devices, e.g., wearable devices that track, report, and communicate various biometric measurements, e.g., distance traveled, steps taken, flights of stairs climbed, etc. Such devices may take the form of a small device that is clipped to a person's clothing or worn on a person's wrist. Such a device may, for example, contain various processors, a printed circuit board, triaxial accelerometers, an altimeter, a display, a vibramotor, a rechargeable battery, a recharging connector, an input button, and a piezoelectric device all within a housing that measures approximately 2" in length, 0.75" wide, and 0.3" thick. A hybrid piezoelectric device/RF antenna may be used in such a device to provide a more compact packaging solution.

Due to the small size of such devices, a hybrid antenna such as those discussed herein may provide the ability to offer a more compact communications solution than might otherwise be possible, allowing additional volume within the housing to be made available for other purposes. Such dimensions may prove to be particularly well-suited to RF communications in the Bluetooth wireless protocol bands, e.g., 2402 MHz to 2480 MHz.

Hybrid antennas that support other wireless communications protocols may also be designed using the principles outlined herein. For example, the hybrid antenna may be dimensioned to be suitable for use with Long Term Evolution (LTE) frequency bands or other cellular communications protocol bands, GPS frequency bands, ANT, 802.11, and ZigBee, for example, as well as frequency bands associated with other communications standards. The RF radiator size, piezoelectric assembly size, first distance, first gap, degree of overlap between the RF radiator and the piezoelectric assembly, and other parameters discussed herein may be adjusted as needed in order to produce a hybrid antenna, as described herein, that is compatible with such other frequency bands.

Hybrid antennas, as disclosed herein, lend themselves to a variety of packaging options. FIGS. 4A through 4E depict a number of packaging variations for a hybrid antenna as disclosed herein. Each of these figures shows a small electronic device, e.g., the housing or housing components for a wrist-mounted fitness monitoring device, and various representative internal components.

FIG. 4A depicts a schematic side view (left) and side exploded view (right) of one configuration of an example device housing and hybrid piezoelectric device/RF antenna. Visible in FIG. 4A is a PCB 450, a display 452, and a battery 448. A carrier element 442 is also shown; an RF radiator 406 may be mounted to the carrier element 442. The carrier element 442 may act as a non-conductive support structure to support the RF radiator 406; the RF radiator 406 may be a metal component that is clipped or adhered to the carrier element 442, or it may be provided by a metallization pattern created directly on the carrier element 442. The carrier element 442 may be supported by the PCB 450, or may be supported by other components. The RF radiator 406 may be electrically connected to the PCB 450 or other electronics components in order to provide connections between the RF radiator 406 and the antenna feed. The RF radiator 406 may also be electrically connected to a ground plane, e.g., the ground plane of the PCB 450 or another large, conductive structure. Such connections may be provided by lead wires or other conductive paths.

The PCB 450, display 452, battery 448, carrier element 442, and RF radiator 406 may be assembled together and inserted into a cavity formed between a first housing portion 444 and a second housing portion 446. A piezoelectric assembly 412 may be adhered to the exterior surface of the first housing portion 444. When assembled, as shown on the right in FIG. 4A, an air gap and the first housing portion 444 are interposed between the piezoelectric assembly 412 and the RF radiator 406; these elements may define the first gap, as described above. The arrangement of the ground plane and RF radiator 406/piezoelectric assembly 412 in this example is similar to the "flat" configuration described earlier. Although there is some slight angle between the ground plane and the other elements, the resulting assembly is still capable of functioning as a hybrid antenna. In some such implementations, the piezoelectric assembly 412 may be adhered to the carrier element 442 instead of to the first housing portion 444.

FIG. 4B depicts a schematic side view (left) and side exploded view (right) of one configuration of another example device housing and hybrid piezoelectric device/RF antenna.

FIG. 4B depicts an implementation that is largely similar to that shown in FIG. 4A. To avoid needless repetition, the reader is referred to the discussion above regarding FIG. 4A for information regarding the various depicted components. The implementation shown in FIG. 4B differs from that shown in FIG. 4A in that the piezoelectric assembly 412 is adhered to the inside surface of the first housing portion 444 such that the first gap is only occupied by air rather than by air and the first housing portion 412.

Figure 4C:
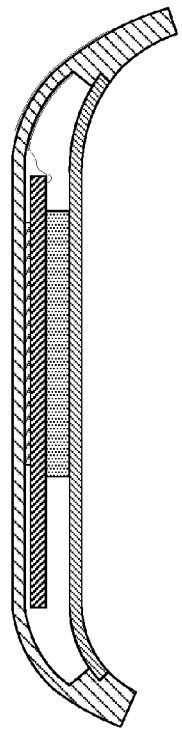
FIG. 4C depicts a schematic side view (left) and side exploded view (right) of one configuration of yet another example device housing and hybrid piezoelectric device/RF antenna.
Figure 4C:
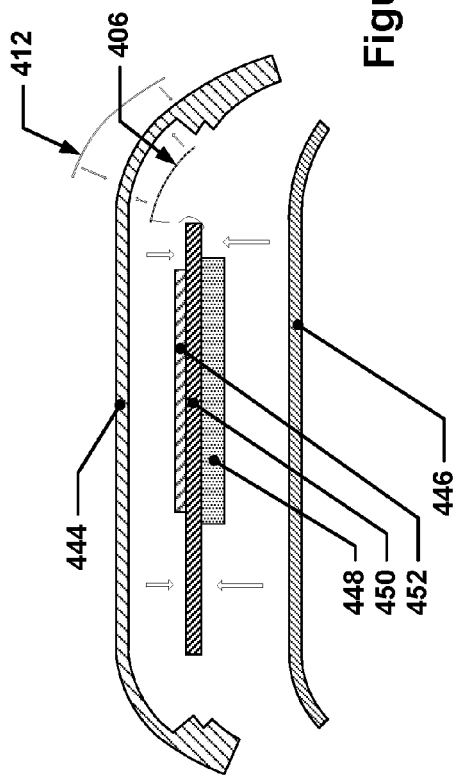

FIG. 4C depicts a schematic side view (left) and side exploded view (right) of one configuration of another example device housing and hybrid piezoelectric device/RF antenna. In FIG. 4C, a slightly different first housing portion 444 and second housing portion 446 are depicted, and the carrier element has been eliminated in favor of mounting the RF radiator 406 directly to the first housing portion 444. The piezoelectric assembly 412 may then be mounted to the opposing surface of the first housing portion 444. When assembled, the first housing portion 444 may be positioned between the RF radiator 406 and the piezoelectric assembly 412.

Figure 4D:
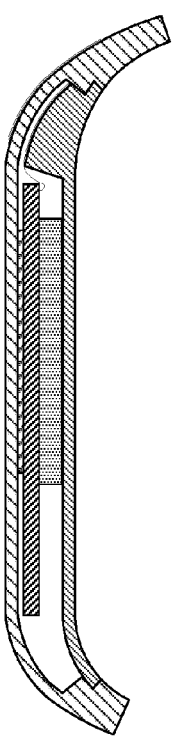
FIG. 4D depicts a schematic side view (left) and side exploded view (right) of one configuration of a further example device housing and hybrid piezoelectric device/RF antenna.
Figure 4D:
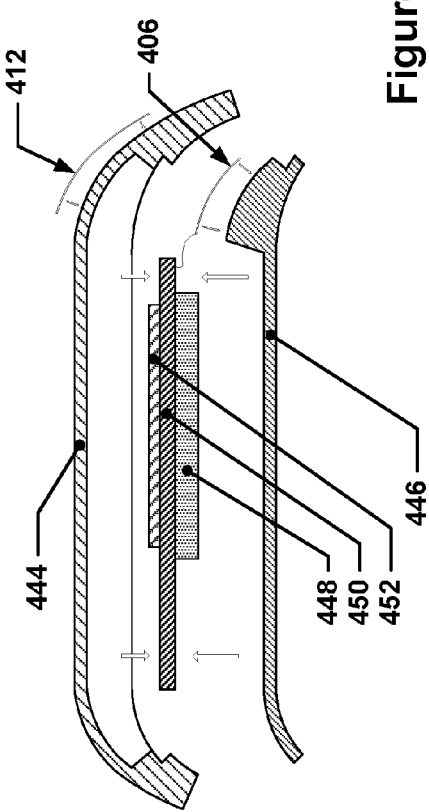

FIG. 4D depicts a schematic side view (left) and side exploded view (right) of one configuration of another example device housing and hybrid piezoelectric device/RF antenna. In FIG. 4D, the second housing portion 446 includes a mounting surface on which the RF radiator 406 may be mounted (or metalized onto). The piezoelectric assembly 412 may be adhered to the exterior surface of the first housing portion 444. When assembled with the first housing portion 444, the second housing portion 446 may position the RF radiator 406 such that a small air gap and a portion of the first housing portion 444 are located in the first gap.

Figure 4E:
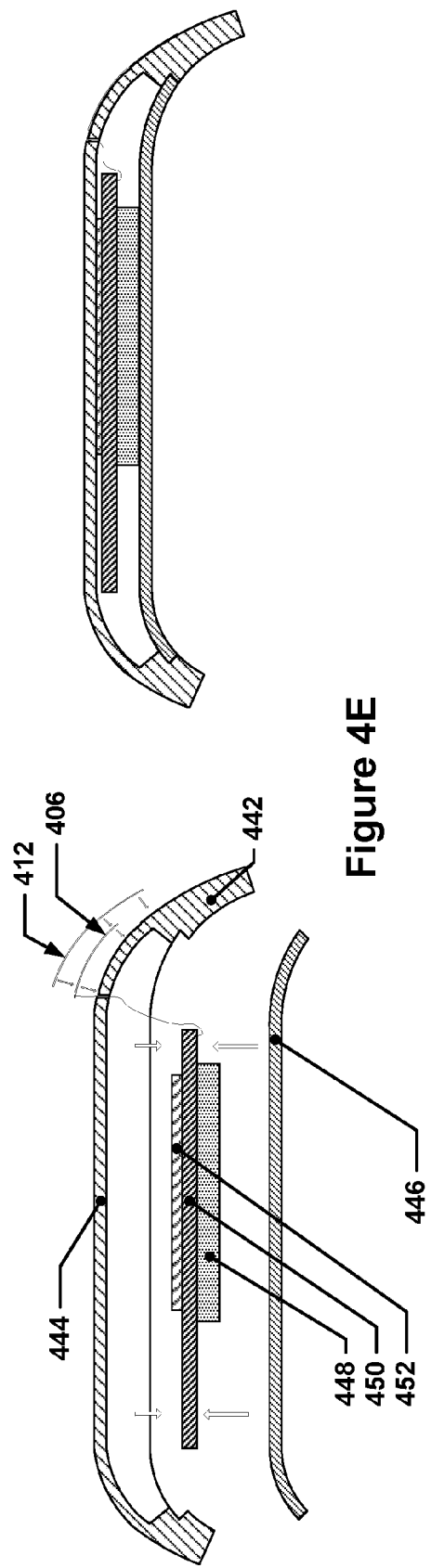
FIG. 4E depicts a schematic side view (left) and side exploded view (right) of one configuration of an additional example device housing and hybrid piezoelectric device/RF antenna.

FIG. 4E depicts a schematic side view (left) and side exploded view (right) of one configuration of another example device housing and hybrid piezoelectric device/RF antenna. In FIG. 4E, the RF radiator 406 may be attached, or metalized onto, the exterior surface of the first housing portion 444. The piezoelectric assembly 412 may then be adhered onto or otherwise connected to the first housing portion with the RF radiator 406 interposed between the piezoelectric assembly 412 and the first housing portion 444. The piezoelectric assembly 412 and the RF radiator 406 may be recessed into a slight recess in the first housing portion 444 if desired. This implementation is similar to the implementation of the hybrid antenna shown in FIGS. 3A and 3B.

These arrangements are only representative arrangements, and various other variations of these components may be practiced in order to provide a hybrid antenna according to the details disclosed herein; such alternatives are also within the scope of this disclosure.

For example, the RF radiator and/or the ground plane may be formed in a variety of other shapes. Examples of alternative shapes for the RF radiator are shown in FIGS. 5A through 6C. Certain implementations of the hybrid antenna may also use these alternative shapes for the ground plane.

Figure 5A:
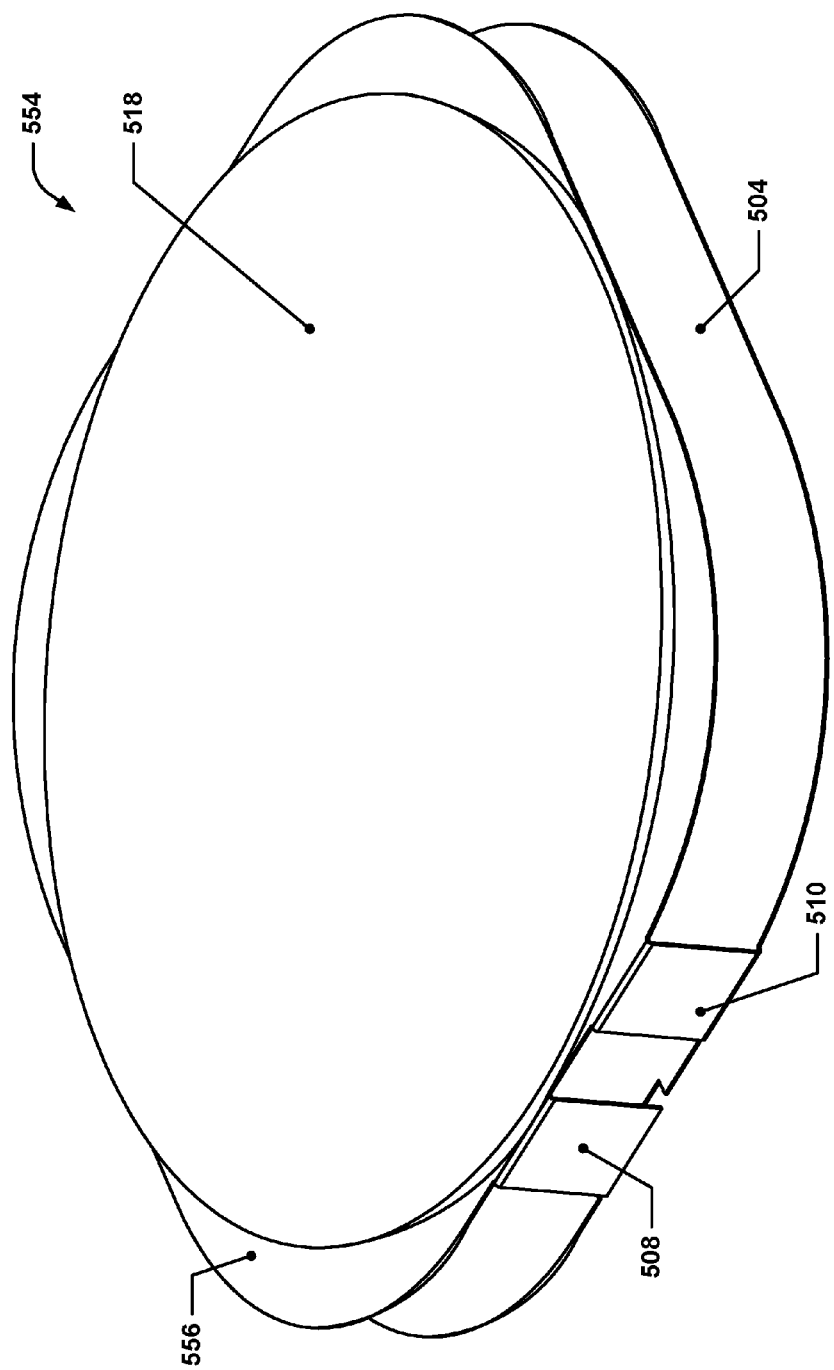
FIG. 5A depicts an alternative example of a hybrid piezoelectric device/RF antenna.

FIG. 5A depicts an alternative example of a hybrid piezoelectric device/RF antenna.

In FIG. 5A, a hybrid antenna 554 includes a piezoelectric assembly 518 that is similar in configuration to the piezoelectric assembly in FIG. 1B. However, packaging requirements in different electric devices may result in hybrid antennas of different shapes. Hybrid antennas may not always take the form of rectangular or box-like shapes. One such implementation of a non-rectangular shaped hybrid antenna is shown in FIG. 5A as, differing from the hybrid antenna implementation in FIG. 1B, the hybrid antenna 554 in FIG. 5A has a substantially circular ground plane 504 and a substantially circular RF radiator 556. "Substantially circular" as described may or may not be fully circular. Rather, a ground plane or RF radiator may be substantially circular as long as there are prominent radiuses on their edges. In the implementation shown in FIG. 5A, the ground plane 504 and the RF radiator 556 are not fully circular as both contain linear portions along their perimeters.

The feed post 508 and the shorting post 510 of the hybrid antenna 554 have been relocated to linear portions of the perimeters of the ground plane 504 and the RF radiator 556 so that the feed post 508 and the shorting post 510 may remain a flat metallic piece. In other implementations, the feed post 508 and the shorting post 510 may be curved or formed into other shapes.

Figure 5B:
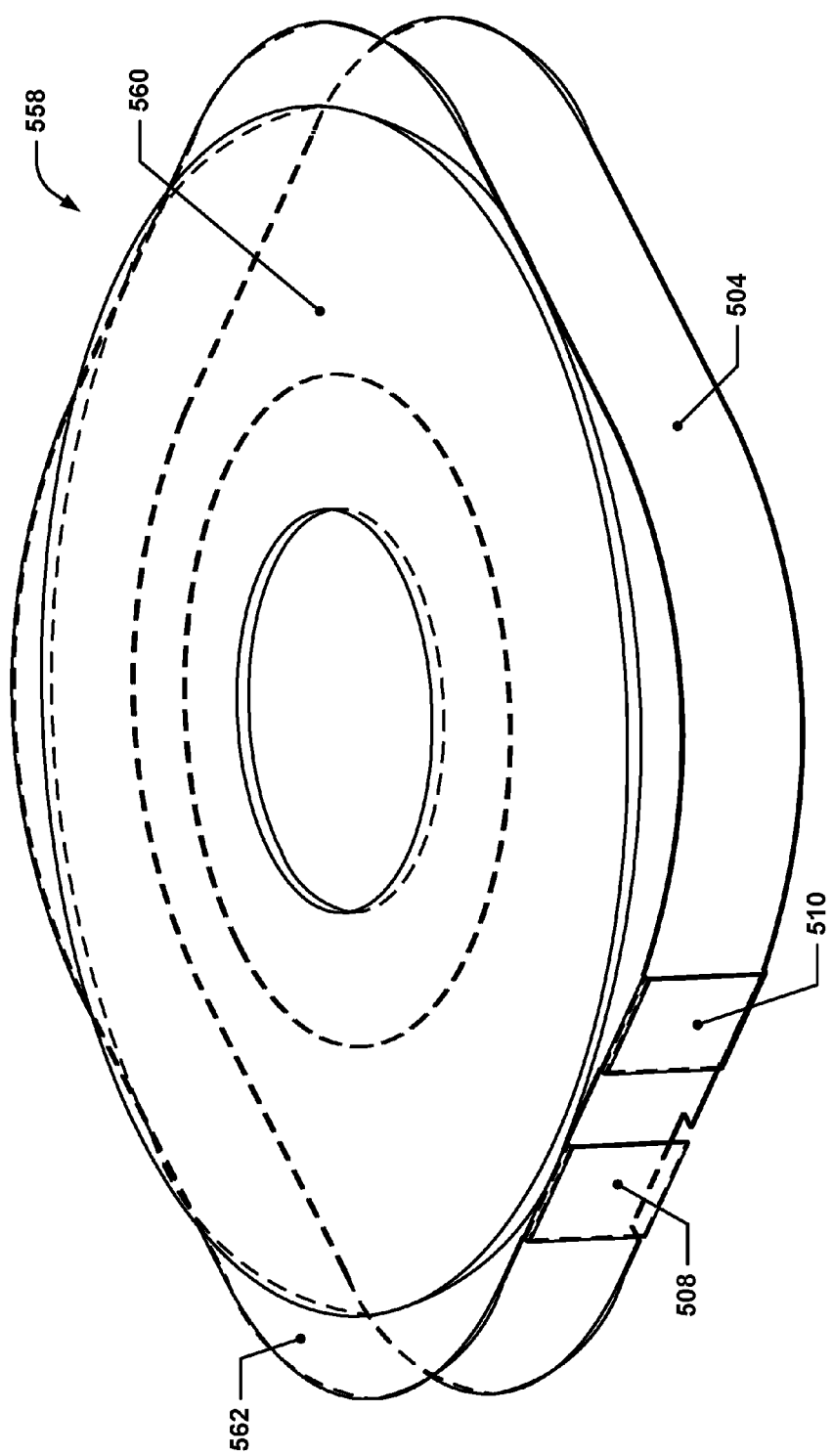
FIG. 5B depicts a further alternative example of a hybrid piezoelectric device/RF antenna.

FIG. 5B depicts a further alternative example of a hybrid piezoelectric device/RF antenna. The hybrid antenna 558 in FIG. 5B is similar in configuration to the hybrid antenna in FIG. 5A.

The hybrid antenna 558 includes a circular piezoelectric assembly 560 and a RF radiator 562 and ground plane 504 that are substantially circular. In contrast to the piezoelectric assembly and the RF radiator of the hybrid antenna shown in FIG. 5A though, the piezoelectric assembly 560 and the RF radiator 562 are O-shaped, i.e., they have holes cut in their centers. Depending on the design requirements of the hybrid antenna, the O-shaped piezoelectric assembly or RF radiator may be beneficial. For example, the piezoelectric assembly may be O-shaped to allow the piezoelectric assembly to vibrate at a certain frequency. There may also be internal packaging considerations that make an O-shaped piezoelectric assembly, RF radiator, and/or ground plane more ideal.

Other configurations of piezoelectric assemblies, RF radiators, or ground planes are also possible. As described in this disclosure, "O-shaped" components include more than just components that have a circular hole cut out in the center. "O-shaped" components may also include components with square, rectangular, polygonal, oval, or other shaped holes that are centered or off-centered on the piezoelectric assembly, the RF radiator, and/or the ground plane. There may also be multiple holes cut into the components. Indeed, perforated patterns may also be possible.

Figure 5C:
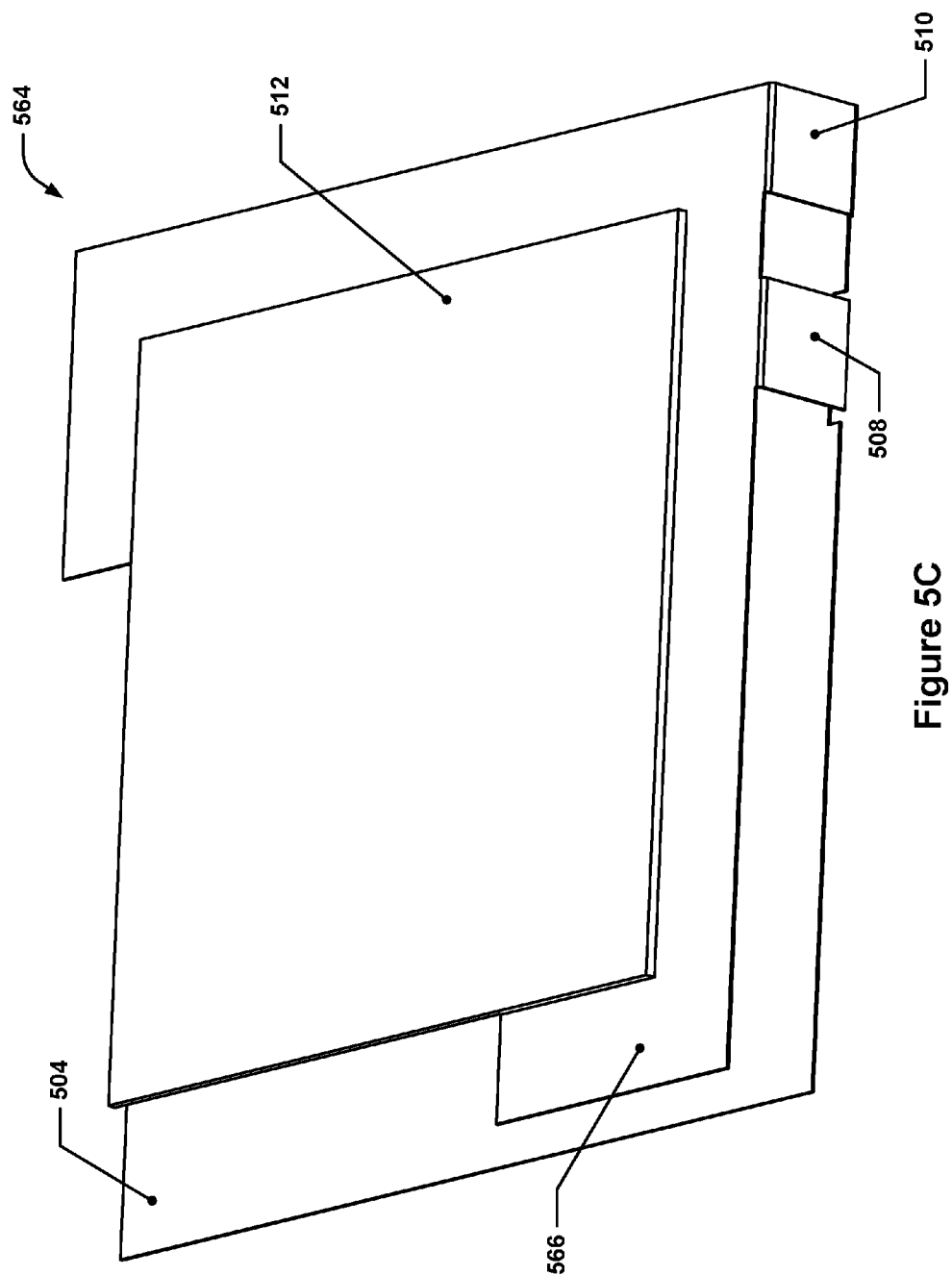
FIG. 5C depicts an additional alternative example of a hybrid piezoelectric device/RF antenna.

FIG. 5C depicts an additional alternative example of a hybrid piezoelectric device/RF antenna. The hybrid antenna 564 is similar in configuration to the hybrid antenna shown in FIG. 1A. However, hybrid antenna 564 has a RF radiator 566 that is L-shaped rather than rectangular like the RF radiator shown in FIG. 1A.

Unlike previous implementations shown, the RF radiator 566 of hybrid antenna 564 only partially overlaps the piezoelectric assembly 512. Various implementations of the hybrid antenna may have RF radiators that overlap the piezoelectric assembly to varying degrees.

In various implementations of the hybrid antenna, the RF radiator and ground plane may be in various shapes. FIG. 6A depicts a top-down view of an example RF radiator with ground plane for use in a hybrid piezoelectric device/RF antenna. The RF radiator 666 of the implementation shown in FIG. 6A is L-shaped, similar to the RF radiator of the hybrid antenna in FIG. 5C. The implementation of the hybrid antenna shown in FIG. 6A also includes a ground plane 604 and a feed post 608.

Figure 6B:
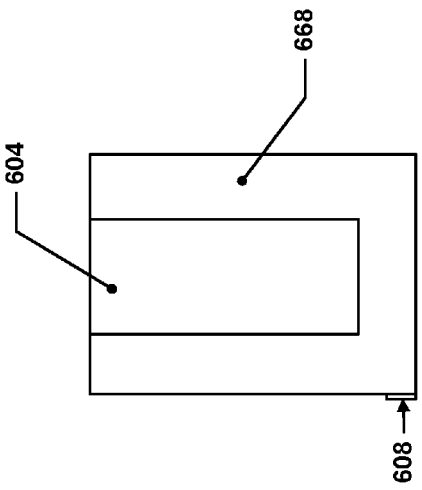
FIG. 6B depicts a top-down view of an additional example RF radiator with ground plane for use in a hybrid piezoelectric device/RF antenna.

FIG. 6B depicts a top-down view of an additional example RF radiator with ground plane for use in a hybrid piezoelectric device/RF antenna. The RF radiator 668 of the implementation shown in FIG. 6B is U-shaped. U-shaped RF radiators, such as RF radiator 668, have at least one concave side. The depth of the concavity of the RF radiator may vary. The implementation of the hybrid antenna shown in FIG. 6B also includes a ground plane 604 and a feed post 608.

Figure 6D:
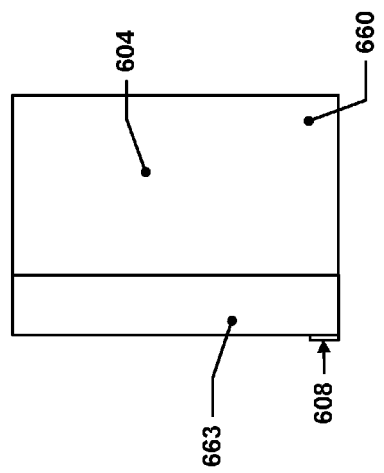
FIG. 6D depicts a top-down view of yet another example RF radiator with ground plane for use in a hybrid piezoelectric device/RF antenna.
Figure 6A:
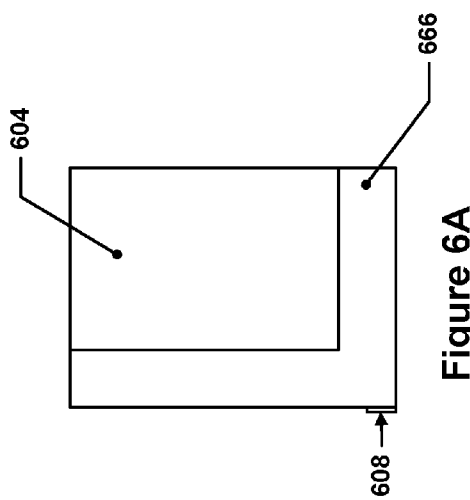
FIG. 6A depicts a top-down view of an example RF radiator with ground plane for use in a hybrid piezoelectric device/RF antenna.
Figure 6C:
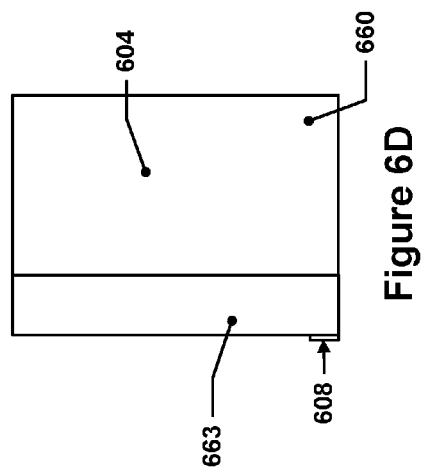
FIG. 6C depicts a top-down view of another example RF radiator with ground plane for use in a hybrid piezoelectric device/RF antenna.

FIG. 6C depicts a top-down view of another example RF radiator with ground plane for use in a hybrid piezoelectric device/RF antenna. The RF radiator 660 is another implementation of an O-shaped RF radiator. An O-shaped RF radiator had previously been described in FIG. 5B. In contrast to the circular cut-out of the O-shaped RF radiator in FIG. 5B, the cut-out of the O-shaped RF radiator 660 in FIG. 6C is rectangular. Other geometries of cut-outs are also possible.

FIG. 6D depicts a top-down view of yet another example RF radiator with ground plane for use in a hybrid piezoelectric device/RF antenna. The RF radiator 663 of the implementation shown in FIG. 6D is I-shaped.

Though FIGS. 6A through 6D describe different variations of possible RF radiator geometries, the same variations and other variations of geometries evident from FIGS. 6A through 6D may be used in other implementations of RF radiators, or may be used in other implementations of ground planes and piezoelectric assemblies. The implementations of the hybrid antennas shown in FIGS. 6A through 6D do not include a shorting post. Other implementations of the hybrid antennas may include a shorting post.

Assembly of the implementations of a hybrid antenna as disclosed herein may include providing an RF radiator, mounting the RF radiator to a first surface of a first housing component, providing a piezoelectric assembly, and mounting the piezoelectric assembly such that the piezoelectric assembly is electrically coupled with the RF radiator. In some such methods, the piezoelectric assembly may have a backing material or insulating layer. In some implementations, the piezoelectric assembly may be bonded to the first surface and the radiator may be interposed between the piezoelectric assembly and the first surface. In some other implementations, a second housing component may be provided and the piezoelectric assembly may be bonded to a second surface on the second housing component. The first housing component and the second housing component may then be assembled together such that the piezoelectric assembly is placed in the proper orientation with respect to the RF radiator in order to produce a hybrid antenna as disclosed herein.

Other methods of assembling a hybrid antenna, such as methods that are evident from FIGS. 4A through 4E, are also within the scope of this disclosure.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein. An antenna with some similar features as the hybrid antenna detailed in this disclosure is described in U.S. patent application Ser. No. 14/290,906, filed May 29, 2014, titled "HYBRID RADIO FREQUENCY/INDUCTIVE LOOP ANTENNA," which is hereby incorporated by reference in its entirety.

What is claimed is:

1. An apparatus comprising:
a ground plane;
a radio-frequency radiator, the radiator offset from the ground plane in a direction substantially normal to the ground plane by a first distance;
a feed post conductively connected to the radiator; and
a piezoelectric assembly offset from the ground plane in a direction substantially normal to the ground plane by a second distance, the piezoelectric assembly configured to couple inductively with the radiator and being separated from the radiator by at least a housing structure of the apparatus, wherein the piezoelectric assembly, the radiator, the ground plane, and the feed post together form an antenna configured to produce electro-magnetic radio-frequency signals and receive electro-magnetic radio-frequency signals.

2. The apparatus of claim 1, wherein:
the piezoelectric assembly comprises a piezoelectric material, a first electrode, and a second electrode,
the piezoelectric material is positioned between the first electrode and the second electrode, and
the piezoelectric assembly is configured to produce a piezoelectric effect and configured to be powered through mutual inductive coupling with the radiator.

3. The apparatus of claim 2, wherein the piezoelectric material includes one or more compounds selected from the group consisting of: gallium orthophosphate, langasite, barium titanate, lead titanate, lead zirconate titanate, lithium niobate, lithium tantalate, sodium tungstate, zinc oxide, $Ba_2NaNb_5O_5$, $Pb_2KNb_5O_{15}$, sodium potassium niobate, bismuth ferrite, sodium niobate, bismuth titanate, sodium bismuth titanate, and polyvinylidene fluoride.

4. The apparatus of claim 1, further comprising a current-blocking component, wherein:
the current-blocking component is configured to at least substantially block radio-frequency current from reaching the piezoelectric assembly; and
the current-blocking component is in conductive contact with the feed post.

5. The apparatus of claim 1, wherein the piezoelectric assembly at least partially overlaps the ground plane.

6. The apparatus of claim 1, wherein the apparatus further comprises an insulating layer that is interposed between the radiator and the piezoelectric assembly.

7. The apparatus of claim 1, further comprising:
a first housing portion; and
a second housing portion, wherein:
the radiator is supported by the first housing portion,
the piezoelectric assembly is supported by the second housing portion, and
the first housing portion is mated to the second housing portion.

8. The apparatus of claim 7, wherein the ground plane is provided by a structure located on an opposite side of the first housing portion from the radiator.

9. The apparatus of claim 8, wherein the structure is selected from the group consisting of: a printed circuit board, a flexible circuit board, a metal plate contained within the apparatus, and a metal plate at least partially providing an exterior surface of the apparatus.

10. The apparatus of claim 1, further comprising:
a plastic carrier; and
a substrate with a printed circuit, wherein:
the radiator is supported by the plastic carrier,
the plastic carrier is supported by the substrate with the printed circuit,
the substrate with the printed circuit acts as the ground plane, and
the piezoelectric assembly is also supported by the plastic carrier.

11. The apparatus of claim 1, wherein the housing structure has a first surface and a second surface, wherein:
the first surface and the second surface are nominally on opposing sides of a portion of the housing structure,
the radiator is formed by a metallization layer deposited on the first surface, and
the piezoelectric assembly is located on or adjacent to the second surface such that the second surface is interposed between the first surface and the piezoelectric assembly.

12. The apparatus of claim 1, wherein the housing structure proximate to the radiator is less than or equal to 2 mm, and wherein the first distance is between about 0.5 mm and 10 mm.

13. The apparatus of claim 1, wherein the piezoelectric assembly is substantially circular or substantially rectangular in overall shape.

14. The apparatus of claim 13, wherein the radiator is substantially circular in overall shape and:
the radiator has an average diameter of between 5 mm and 25 mm; and
the piezoelectric assembly has an average diameter of between 5 mm and 25 mm.

15. The apparatus of claim 1, wherein the radiator is O-shaped, C-shaped, L-shaped, U-shaped, or rectangular-shaped.

16. The apparatus of claim 1, wherein the radiator is configured to couple inductively and directly with the piezoelectric assembly.

17. The apparatus of claim 1, wherein the ground plane is a non-planar surface.

18. The apparatus of claim 1, further comprising:
a first housing portion of a wearable device; and
a second housing portion of the wearable device and mated to the first housing portion, wherein the radiator is supported in a recess between the first housing portion and the second housing portion, the recess being positioned outside a display cover of the wearable device.

19. The apparatus of claim 1, further comprising a shorting post conductively connecting the radiator to the ground plane, wherein:
the piezoelectric assembly, the radiator, the ground plane, the shorting post, and the feed post form an antenna configured to produce and receive electric radio-frequency signals in a Bluetooth-compatible frequency band.

20. The apparatus of claim 1, further comprising a shorting post conductively connecting the radiator to the ground plane, wherein:
the piezoelectric assembly, the radiator, the ground plane, the shorting post, and the feed post form an antenna configured to produce and receive electric radio-frequency signals in a GPS-compatible frequency band.

21. The apparatus of claim 1, wherein the radiator is interposed between the piezoelectric assembly and the ground plane.

22. The apparatus of claim 1, further comprising a first electrical conductor and a second electrical conductor, wherein the piezoelectric assembly comprises a piezoelectric material between a first electrode and a second electrode, the first electrical conductor connected to the first electrode and the second electrical conductor connected to the second electrode.

23. The apparatus of claim 1, wherein the piezoelectric assembly is configured to produce a sound or range of sounds.

24. The apparatus of claim 1, further comprising a battery, wherein the piezoelectric assembly is configured to scavenge energy by converting vibrations induced in the piezoelectric assembly into an electrical charge and output the electrical charge to the battery.

25. The apparatus of claim 1, wherein the antenna is a planar inverted-F antenna (PIFA).

26. A method comprising:
   a) providing a radio-frequency radiator, a ground plane, and a feed post, wherein the radiator is separated from the ground plane by a first distance, and wherein the feed post is conductively connected to the radiator;
   b) mounting the radiator to a first surface of a first housing component;
   c) providing a piezoelectric assembly; and
   d) placing the piezoelectric assembly such that the piezoelectric assembly is offset from the ground plane in a direction substantially normal to the ground plane by a second distance, and is configured to couple inductively with the radiator and is separated from the radiator by at least a housing structure but sufficiently close to the radiator to be coupled with the radiator, wherein the piezoelectric assembly, the radiator, the ground plane, and the feed post together form an antenna configured to produce electro-magnetic radio-frequency signals and receive electro-magnetic radio-frequency signals.

27. The method of claim 26, wherein the radiator is interposed between the piezoelectric assembly and the ground plane, the piezeoelectric assembly configured to be powered through mutual inductive coupling with the radiator.

28. The method of claim 26, further comprising:
   providing a second housing component;
   bonding the piezoelectric assembly to a second surface of the second housing component; and
   mating the second housing component to the first housing component, wherein the piezoelectric assembly is bonded to the second surface in a location that causes (d) to be concurrently performed when the second housing component is mated to the first housing component.

29. The method of claim 28, wherein a recess between the first housing component and the second housing component is defined when the first housing component and the second housing component are mated together, wherein the radiator is supported in the recess.

* * * * *